United States Patent [19]
Phillips et al.

[11] Patent Number: 5,990,317
[45] Date of Patent: *Nov. 23, 1999

[54] 2-(1H-4(5)-IMIDAZOYL) CYCLOPROPYL COMPOUNDS

[75] Inventors: James G. Phillips, Bay Village; Clark E. Tedford, South Russel; Amin Mohammed Khan, Solon, all of Ohio

[73] Assignee: Gliatech, Inc., Cleveland, Ohio

[*] Notice: This patent is subject to a terminal disclaimer.

[21] Appl. No.: 08/945,915

[22] PCT Filed: May 29, 1996

[86] PCT No.: PCT/US96/07833

§ 371 Date: Feb. 6, 1998

§ 102(e) Date: Feb. 6, 1998

[87] PCT Pub. No.: WO96/38141

PCT Pub. Date: Dec. 5, 1996

Related U.S. Application Data

[63] Continuation-in-part of application No. 08/453,359, May 30, 1995, Pat. No. 5,652,258.

[51] Int. Cl.⁶ .................. C07D 233/64; C07D 233/56; A61K 31/415
[52] U.S. Cl. .................. 548/338.1; 514/400; 548/340.1; 548/341.1; 548/341.5; 548/342.1; 548/345.1
[58] Field of Search ............... 548/345.1, 338.1, 548/340.1, 341.1, 341.5, 342.1; 514/400

[56] References Cited

U.S. PATENT DOCUMENTS

| | | | |
|---|---|---|---|
| 4,707,487 | 11/1987 | Arrang et al. | 514/326 |
| 5,217,986 | 6/1993 | Pomponi et al. | 514/408 |
| 5,290,790 | 3/1994 | Arrang et al. | 514/326 |
| 5,652,258 | 7/1997 | Phillips et al. | 514/400 |

*Primary Examiner*—Floyd D. Higel
*Attorney, Agent, or Firm*—Rockey, Milnamow & Katz

[57] ABSTRACT

The present invention provides compounds having $H_3$ histamine receptor antagonist activity of formula (1.0) wherein $R_2$ is a hydrogen or a methyl or ethyl group; $R_3$ is a hydrogen or a methyl or ethyl group; n is 0, 1, 2, 3, 4, 5, or 6; and $R_1$ is selected from the group consisting of (a) $C_3$ to $C_8$ cycloalkyl; (b) phenyl or substituted pneyl; (c) alkyl; (d) heterocyclic; (e) decahydronaphthalene; and (f) octahydroindene; with the proviso that when X is H, A can be —$CH_2CH_2$—, —$COCH_2$—$CON(CH_3)$—, —CH=CH—, α, —$CH_2$—NH—, —$CH_3$—$N(CH_3)$—, —CH(OH)$CH_2$—, —NH—$CH_2$—, —$N(CH_3)$—$CH_2$—, —$CH_2O$—, —$CH_2S$—, and —NHCOO—; when X is $NH_2$, $HN(CH_3)$, $N(CH_3)_2$, OH, $OCH_3$, $CH_3$, SH and $SCH_3$; A can be —NHCO—, —$N(CH_3)$—CO—, —$NHCH_2$—, —$N(CH_3)$—$CH_2$—, —CH=XH—, —$COCH_2$—, —$CH_2CH_2$—, —CH( )H)$CH_2$—, or β; and when $R_1$ and X taken together denote a 5,6 or 6,6 saturated bicyclic ring structure, X can be NH, O, or S. The pharmaceutically acceptable salts, hydrates, and individual stereoisomers of compounds of structural formula (1.0), as well as mixtures thereof, are also contemplated as falling within the scope of the present invention. The invention also provides pharmaceutical compositions comprising a pharmaceutically acceptable carrier in combination with an effective amount of a compound of said formula and a method of treating conditions in which antagonism of histamine $H_3$ receptors may be of therapeutic importance.

(1.0)

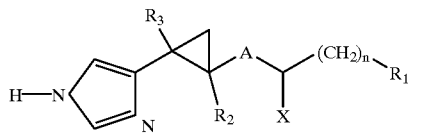

(α)

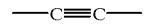

(β)

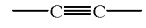

15 Claims, No Drawings

2-(1H-4(5)-IMIDAZOYL) CYCLOPROPYL COMPOUNDS

CROSS-REFERENCE TO RELATED APPLICATIONS

This application is a Section 371 application of PCT Application Serial No. PCT/US96/07833, filed May 29, 1996, which is a continuation-in-part application of U.S. patent application Ser. No. 08/453,359, filed May 30, 1995, now U.S. Pat. No. 5,652,258.

TECHNICAL FIELD

This invention relates to compounds having pharmacological activity, to compositions containing these compounds, and to a method of treatment employing the compounds and compositions. More particularly, this invention concerns certain 2-(1H-4(5)-imidazoyl)cyclopropyl derivatives and their salts or solvates. These compounds have $H_3$ histamine receptor antagonist activity. This invention also relates to disorders in which histamine $H_3$ receptor blockade is beneficial.

BACKGROUND OF THE INVENTION

Histamine is a chemical messenger involved in various complex biological actions. When released, histamine interacts with specific macromolecular receptors on the cell surface or within a target cell to elicit changes in many different bodily functions. Various cell types including smooth muscle, blood cells, cells of the immune system, endocrine and exocrine cells as well as neurons respond to histamine by stimulating the formation of intracellular signals, including formation of phosphatidylinositol or adenylate cyclase. Evidence that histamine plays a role as a neurotransmitter was established by the mid to late 1970's (Schwartz, 1975) *Life Sci.* 17: 503–518. Immunohistochemical studies identified histaminergic cell bodies in the tuberomammillary nucleus of the posterior hypothalamus with widespread projections in the dicencephalon and telencephalon (Inagaki et al., 1988) *J. Comp. Neurol.* 273: 283–300.

Identification of two histamine receptors ($H_1$ and $H_2$) was reported to mediate the biochemical actions of histamine on neurons. Recently, studies have demonstrated the existence of a third subtype of histamine receptor, the histamine $H_3$ receptor (Schwartz et al., 1986) *TIPS* 8: 24–28. Various studies have now demonstrated that histamine $H_3$ receptors are found on the histaminergic nerve terminals in the brains of several species, including man (Arrang et al., 1983) *Nature* 302: 832–837. The $H_3$ receptor found on the histaminergic nerve terminal was defined as an autoreceptor and could intimately control the amount of histamine released from the neurons. Histamine, the natural compound, was capable of stimulating this autoreceptor but when tested against known $H_1$ and $H_2$ receptor agonists and antagonists, a distinct pharmacological profile emerged. Further $H_3$ receptors have been identified on cholinergic, serotoninergic and monoamine nerve terminals in the peripheral nervous system (PNS) and central nervous system including the cerebral cortex and cerebral vessels. These observations suggest that $H_3$ receptors are uniquely located to modulate histamine as well as other neurotransmitter release, and $H_3$ antagonists could be important mediators of neuronal activity.

As stated, CNS histaminergic cell bodies are found in the magnocellular nuclei of the hypothalamic mammillary region and these neurons project diffusely to large areas of the forebrain. The presence of histaminergic cell bodies in the tuberomammillary nucleus of the posterior hypothalamus, a brain area involved in the maintenance of wakefulness, and their projections to the cerebral cortex suggest a role in modulating the arousal state or sleep-wake. The histaminergic projection to many limbic structures such as the hippocampal formation and the amygdaloid complex suggest roles in functions such as autonomic regulation, control of emotions and motivated behaviors, and memory processes.

The concept that histamine is important for the state of arousal, as suggested by the location of histaminergic pathways, is supported by other types of evidence. Lesions of the posterior hypothalamus is well known to produce sleep. Neurochemical and electrophysiological studies have also indicated that the activity of histaminergic neurons is maximal during periods of wakefulness and is suppressed by barbiturates and other hypnotics. Intraventricular histamine induces the appearances of an arousal EEG pattern in rabbits and increased spontaneous locomotor activity, grooming and exploratory behavior in both saline and pentobarbital-treated rats.

In contrast, a highly selective inhibitor of histidine decarboxylase, the sole enzyme responsible for histamine synthesis, has been shown to impair waking in rats. These data support the hypothesis that histamine may function in modulating behavioral arousal. The role of the $H_3$ receptor in sleep-waking parameters has been recently demonstrated (Lin et al., 1990) *Brain Res.* 529: 325–330. Oral administration of RAMHA, an $H_3$ agonist, caused a significant increase in deep slow wave sleep in the cat. Conversely, thioperamide, an $H_3$ antagonist, enhanced wakefulness in a dose-dependent fashion. Thioperamide has also been shown to increase wakefulness and decrease slow wave and REM sleep in rats. These findings are consistent with in vivo studies demonstrating that thioperamide caused an increase in synthesis and release of histamine. Together, these data demonstrate that selective $H_3$ antagonists may be useful in the treatment of arousal states and sleep disorders.

Serotonin, histamine and acetylcholine have all been demonstrated to be diminished in the Alzheimer's (AD) brain. The histamine $H_3$ receptor has been demonstrated to regulate the release of each of these neurotransmitters. An $H_3$ receptor antagonist would therefore be expected to increase the release of these neurotransmitters in brain. Since histamine has been demonstrated to be important in arousal and vigilance, $H_3$ receptor antagonists might enhance arousal and vigilance via increasing levels of neurotransmitter release and improve cognition. Thus, the use of $H_3$ receptor antagonists in AD, attention deficit hyperactive disorders (ADHD), age-related memory dysfunction and other cognitive disorders would be supported.

$H_3$ receptor antagonists may be useful in treating several other CNS disorders. It has been suggested that histamine may be involved in the control of sleep/wake states as well as states of arousal and alertness, cerebral circulation, energy metabolism, and hyopthalmic hormone secretion. Recent evidence has indicated the possible use of $H_3$ antagonists in the treatment of epilepsy. Work has demonstrated an inverse correlation between the duration of clonic convulsions and brain histamine levels. Thioperamide, an $H_3$ antagonist, was also shown to significantly and dose-dependently decrease the durations of every convulsive phase after electrically-induced convulsions and increase the electroconvulsive threshold.

In spite of their low density, $H_3$ receptor binding sites can be detected outside the brain. Several studies have revealed the presence of $H_3$ heteroreceptors in the gastrointestinal tract, as well as upon neurons of the respiratory tract. Accordingly, an $H_3$ receptor antagonist may be useful in the treatment of diseases and conditions such as asthma, rhinitis, airway congestion, inflammation, hyper and hypo motility and acid secretion of the gastrointestinal tract. Peripheral or central blockade of $H_3$ receptors may also contribute to changes in blood pressure, heart rate and cardiovascular output and could be used in the treatment of cardiovascular diseases.

U.S. Pat. No. 4,707,487 discloses compounds of the general formula:

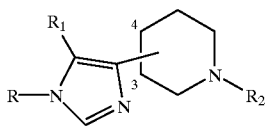

in which $R_1$ denotes H, $CH_3$, or $C_2H_5$, R denotes H or $R_2$ and $R_2$ denotes an alkyl, piperonyl, 3-(1-benzimidazolonyl)-propyl group; a group of formula:

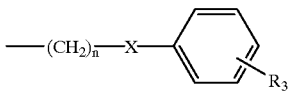

in which n is 0, 1, 2, or 3, X is a single bond or alternatively —O—, —S—, —NH—, —CO—, —CH=CH— or

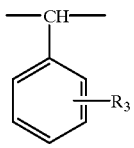

and $R_3$ is H, $CH_3$, F, CN or an acyl group; or alternatively a group of the formula:

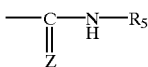

in which Z denotes an O or S atom or a divalent group NH, N—$CH_3$, or N—CH, and $R_5$ denotes an alkyl group, a cycloalkyl group which can bear a phenyl substituent, a phenyl group which can bear a $CH_3$ of F substituent, a phenylalkyl ($C_1$–$C_3$) group or a naphthyl, adamantyl, or p-toluenesulphonylgroup. It is also disclosed that these compounds antagonize the histamine $H_3$ receptors and increase the rate of renewal of cerebral histamine.

WO 92/15567 discloses compounds of general formula:

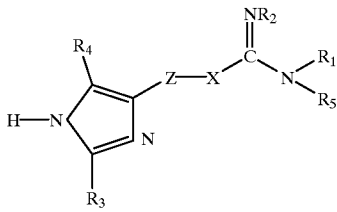

wherein: Z is a group of formula $(CH_2)m$, wherein m=1–5 or a group of the formula:

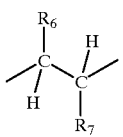

wherein $R_6$=($C_1$–$C_3$) alkyl, $R_7$=($C_1$–$C_3$) alkyl; X represents S, NH, or $CH_2$; $R_1$ represents hydrogen, ($C_1$–$C_3$) alkyl-, aryl ($C_1$–$C_{10}$) alkyl-, wherein aryl may optionally be substituted, aryl, ($C_5$–$C_7$) cycloalkyl, ($C_1$–$C_{10}$) alkyl-, or a group of the formula:

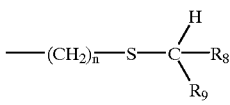

wherein n=1–4 $R_8$ is aryl, aryl ($C_1$–$C_{10}$)alkyl-, ($C_5$–$C_7$) cycloalkyl- or ($C_5$–$C_7$) cycloalkyl ($C_1$–$C_{10}$) alkyl-, and $R_9$ is hydrogen, ($C_1$–$C_{10}$) alkyl- or aryl; $R_2$ and $R_5$ represents hydrogen, ($C_1$–$C_3$) alkyl-, aryl or arylalkyl-, wherein aryl may optionally be substituted; $R_3$ represents hydrogen, ($C_1$–$C_3$) alkyl, aryl, or arylalkyl-, wherein aryl may be substituted; and $R_4$ represents hydrogen, amino-, nitro-, cyano-, halogen-, ($C_1$–$C_3$) alkyl, aryl, or arylalkyl-, wherein aryl may optionally be substituted; wherein aryl is phenyl, substituted phenyl, naphthyl, substituted naphthyl, pyridyl or substituted pyridyl. These compounds are reported to have agonistic or antagonistic activity on the histamine $H_3$ receptor.

U.S. Pat. No. 5,217,986 discloses compounds of formula:

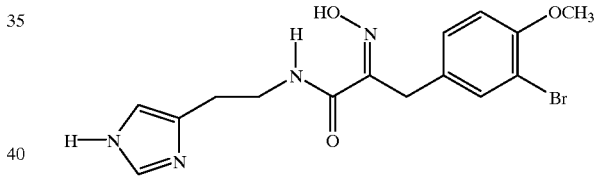

This compound is reported to be active in an $H_3$ receptor assay, is reported to be an $H_3$ antagonist on guinea pig ileum, and accordingly is said to be useful in the treatment of diseases and conditions such as asthma, rhinitis, airway congestion, inflammation, cardiac arrhythmias, hypertension, hyper and hypo motility and acid secretion of the gastrointestinal tract, hypo and hyper-activity of the central nervous system, migraine, and glaucoma.

WO 93/14070 discloses compounds of general formula:

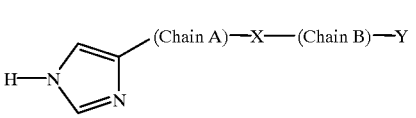

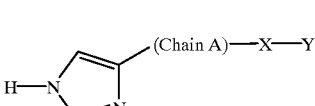

Chain A represents a hydrocarbon chain, saturated or unsaturated, of 1–6 carbon atoms in length; X represents —O—, —S—, —NH—, —NHCO—, —NHCONH—, —NH—CS—NH—, —NHCS—, —O—CO—, —CO—

O—, —OCONH—, —OCON(alkyl)-, —OCONH—CO—, —CONH—, —CON(alkyl)-, —SO—, —CO—, —CHOH—, —NR—C(=NR")—NR—, R and R' can be hydrogen or alkyl and R" is hydrogen or cyano, or $COY_1$, $Y_1$ is alkoxy radical. Chain B represents an alkyl group —$(CH_2)_n$—, n=0–5 or an alkyl chain of 2–8 carbon atoms interrupted by an oxygen or sulfur atom or a group like —$(CH_2)_n$—O— or —$(CH_2)_n$—S— wherein n=1 or 2. Y represents $(C_1-C_8)$ alkyl, $(C_3-C_6)$ cycloalkyl, bicycloalkyl, aryl, cycloalkenyl, heterocycle.

U.S. Pat. No. 5,290,790 discloses compounds of the same general structure as 4,707,487:

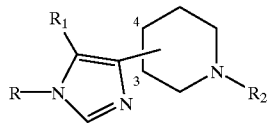

but specifically includes amides wherein $R_2$ is CO—NR'R" and R"R" are independently selected from the group consisting of (a) hydrogen; (b) phenyl or substituted phenyl; (c) alkyl; (d) cycloalkyl; and (e) alkylcycloalkyl such as cyclohexylmethyl or cyclopentylethyl.

The present invention provides, in its principal aspect, compounds of the general formula:

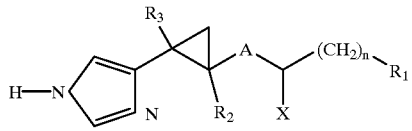

where $R_2$ is a hydrogen or a methyl or ethyl group;
$R_3$ is a hydrogen or a methyl or ethyl group;
n is 0, 1, 2, 3, 4, 5, or 6; and
$R_1$ is selected from the group consisting of (a) $C_3$ to $C_8$ cycloalkyl; (b) phenyl or substituted phenyl; (c) alkyl; (d) heterocyclic; (e) decahydronapthalene; and (f) octahydroindene;
with the proviso that
when X is H, A can be —$CH_2CH_2$—, —$COCH_2$—, —CONH—, —$CON(CH_3)$—, —CH=CH—, —C≡C—, —$CH_2$—NH—, —$CH_2$—$N(CH_3)$—, —CH(OC)$CH_2$—, —NH—$CH_2$—, —$N(CH_3)$—$CH_2$—, —$CH_2$O—, —$CH_2$S—, or —NHCOO—;
when x is $HN_2$, $NC(CH_3)$, $N(CH_3)_2$—, OH, $OCH_3CH_3$, SH, or $SCH_3$; A can be —NHCO—, —$N(CH_3)$—CO—, —$NHCH_2$—, —$N(CH_3)$—$CH_2$—, —CH=CH—, —$COCH_2$—, —$CH_2CH_2$—, —CH(OH)$CH_2$—, or —C≡C—; and
when $R_1$ and X taken together denote a 5,6 or 6,6 saturated bicyclic ring structure X can be NH, O, or S.

The pharmaceutically acceptable salts, hydrates and individual stereoisomers of compounds of the structural formula (1.0) above, as well as mixtures thereof, are also contemplated as falling within the scope of the present invention.

This invention also provides pharmaceutical compositions comprising a pharmaceutically acceptable carrier in combination with an effective amount of a compound of formula (1.0).

The present invention also provides a method of treating conditions in which antagonism of histamine $H_3$ receptors may be of therapeutic importance such as allergy, inflammation, cardiovascular disease (i.e., hyper or hypotension), gastrointestinal disorders (acid secretion, motility) and CNS disorders involving attention or cognitive disorders (i.e., Alzheimer's, Attention Deficit Hyperactive Disorder, age-related memory dysfunction, stroke, etc.), psychiatric and motor disorders (i.e., depression, schizophrenia, obsessive-compulsive disorders, tourette's, etc.) and sleep disorders (i.e., narcolepsy, sleep apnea, insomnia, disturbed biological and circadian rhythms, hyper and hyposomnolence, and related sleep disorders), epilepsy, hypothalamic dysfunction (i.e., eating disorders such as obesity, anorexia/bulimia, thermoregulation, hormone release) comprising administering an effective amount of a compound of formula (1.0) to a patient in need of such treatment.

DETAILED DESCRIPTION OF THE INVENTION

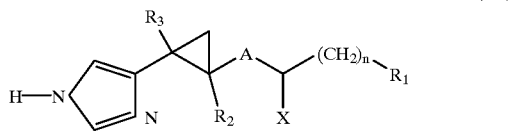

(1.0)

Preferably for compounds of formula (1.0); the cyclopropane attended at the 4(5)-position of the imidazole ring has the trans configuration and when X is H, A can be —$CH_2CH_2$—, —$COCH_2$—, —COHN—, —$CON(CH_3)$—, —CH=CH—, —C≡C—, —$CH_2$—NH—, —$CH_2$—$N(CH_3)$—, —CH(OH)$CH_2$—, —NH—$CH_2$—, —$N(CH_3)$—$CH_2$—, —$CH_2$O—, —$CH_2$S—, or —NHCOO—;

$R_2$ is a hydrogen or a methyl or ethyl group;
$R_3$ is a hydrogen or a methyl or ethyl group;
n is 0, 1, 2, 3, 4, 5, or 6; and
$R_1$ is selected from the group consisting of (a) $C_3$ to $C_8$ cycloalkyl; (b) phenyl or substituted phenyl; (c) alkyl; (d) heterocyclic; (e) decahydronapthalene; and (f) octahydroindene;
when X is $NH_2$, $NH(CH_3)$, $N(CH_3)_2$, OH, $OCH_3$, $CH_3$, SH, and $XCH_3$; A can be —NHCO—, —$N(CH_3)$—CO—, —$NHCH_2$—, —$N(CH_3)$—$CH_2$—, —CH=CH—, —$COCH_2$—, —$CH_2CH_2$—, —CH(OH)$CH_2$, or —C≡C—;

$R_2$ is a hydrogen or a methyl or ethyl group;
$R_3$ is a hydrogen or a methyl or ethyl group;
n is 0, 1, 2, 3, 4, 5, or 6;
$R_1$ is selected from the group consisting of (a) $C_3$ to $C_8$ cycloalkyl; (b) phenyl or substituted phenyl; (c) alkyl; (d) heterocyclic; (e) decahydronapthalene; and (f) octahydroindene;
when $R_1$ and X taken together denote a 5,6 or 6,6 saturated bicyclic ring structure
X can be NH, O, or S; and
when X is constrained in a 5,6 or 6,6 saturated bicyclic ring structure, for example, when X=NH, $R_1$ and X taken together mean an octahydroindole ring structure directly attached to A.

More preferably, the present invention provides compounds of the general formula:

(1.0)

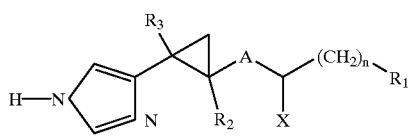

where A is —CONH—, —CH=CH—, —NHCOO—, or —C≡C—;

X is H or $NH_2$;

$R_2$ and $R_3$ are H;

n is 0, 1, 2 or 3;

$R_1$ is $C_6$ cyclohexyl, phenyl or substituted phenyl.

The pharmaceutically acceptable salts, hydrates and individual stereoisomers of compounds of structural formula (1.0) above, as well as mixtures thereof, are also contemplated as falling within the scope of the present invention.

Representative compounds of this invention include compounds of the formulae (2.0) through (51.0):

(2.0)
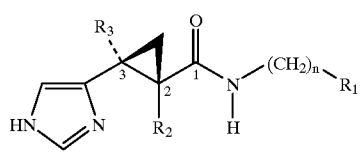

(3.0)
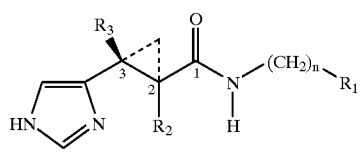

(4.0)
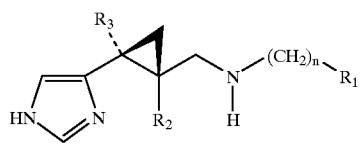

(5.0)
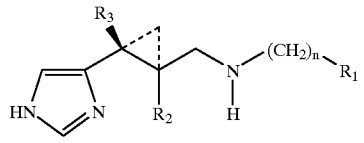

(6.0)
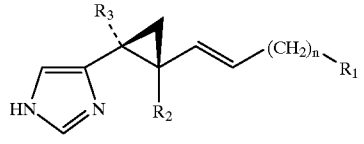

(7.0)
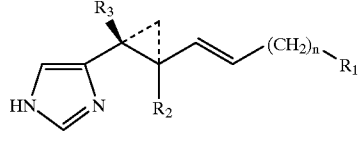

-continued (8.0)
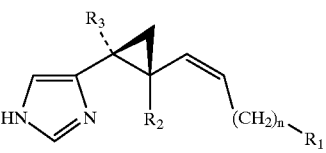

(9.0)
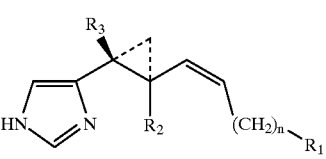

(10.0)
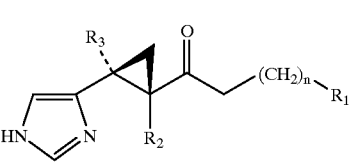

(11.0)
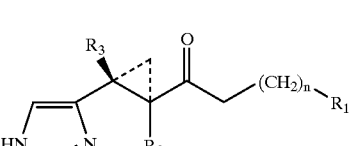

(12.0)
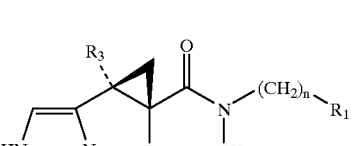

(13.0)
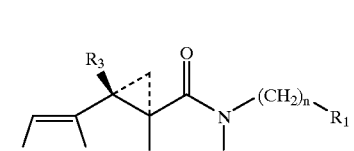

(14.0)
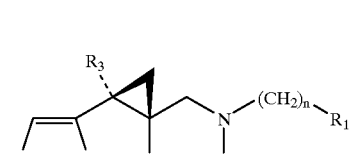

(15.0)
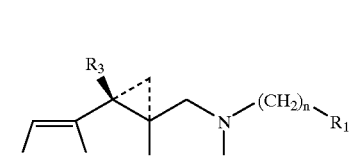

(16.0)
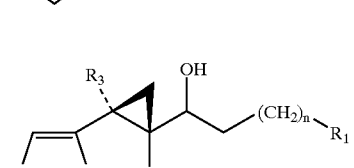

-continued
(17.0)
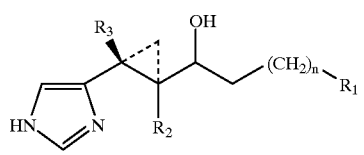
(18.0)
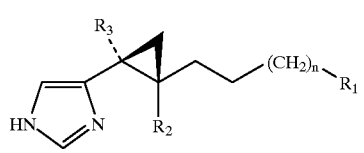
(19.0)
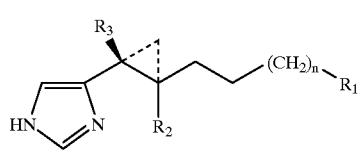
(20.0)
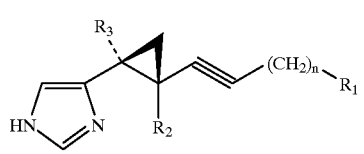
(21.0)
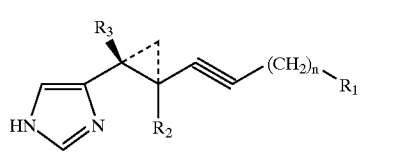
(22.0)
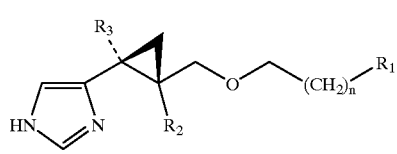
(23.0)
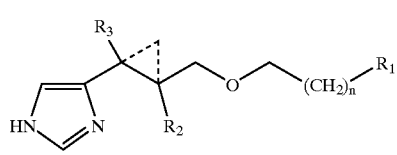
(24.0)
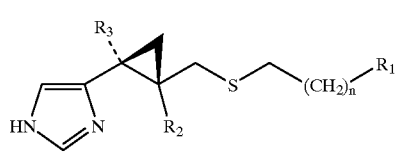
(25.0)
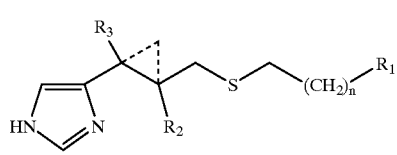
-continued
(26.0)
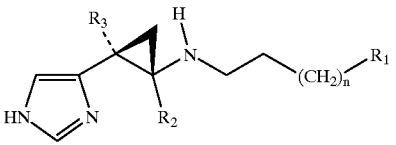
(27.0)
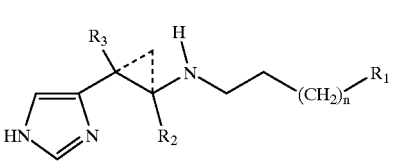
(28.0)
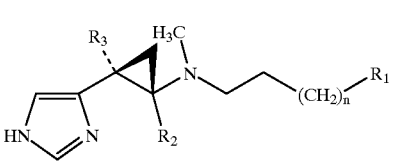
(29.0)
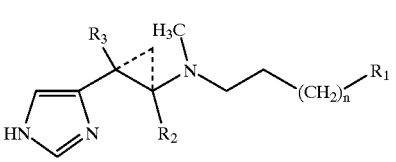
(30.0)
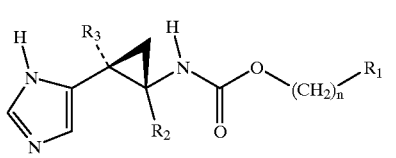
(31.0)
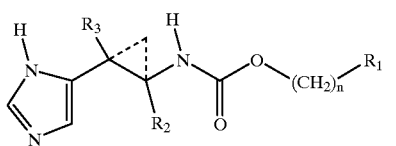
(32.0)
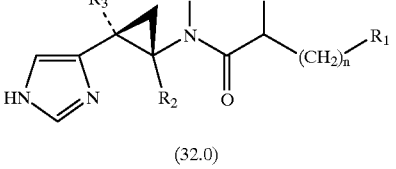
(33.0)
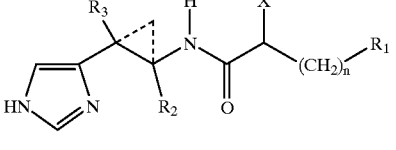
(34.0)
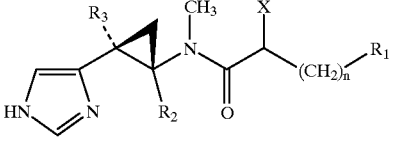

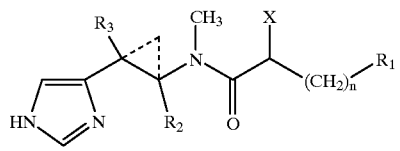
(35.0)
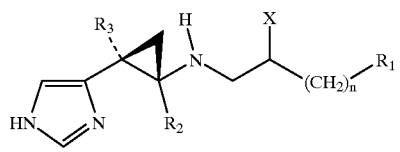
(36.0)
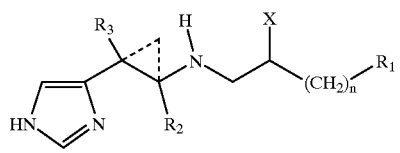
(37.0)
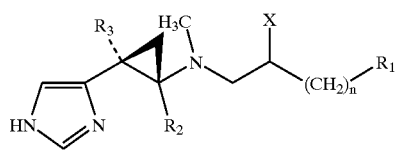
(38.0)
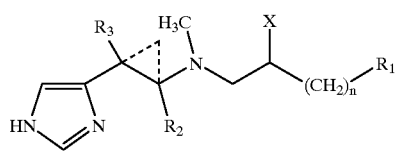
(39.0)
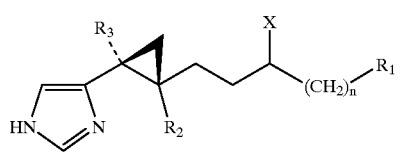
(40.0)
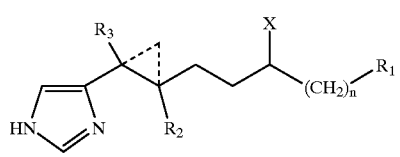
(41.0)
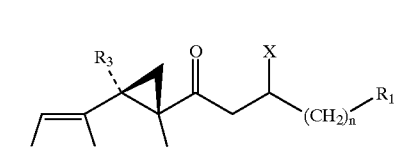
(42.0)
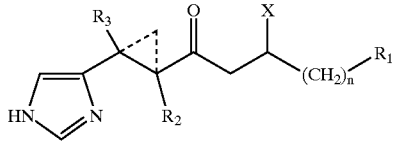
(43.0)
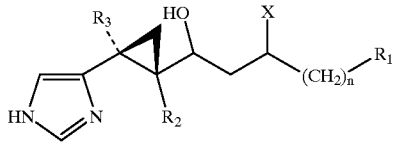
(44.0)
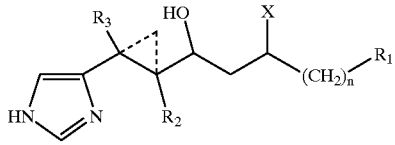
(45.0)
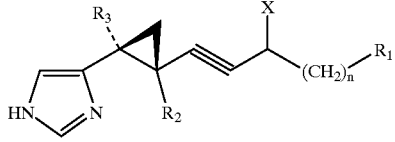
(46.0)
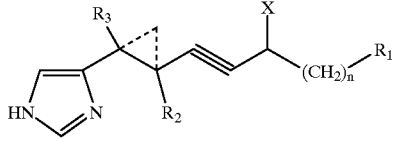
(47.0)
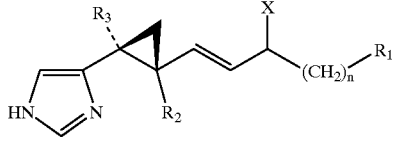
(48.0)
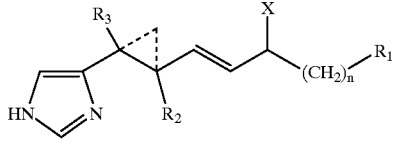
(49.0)
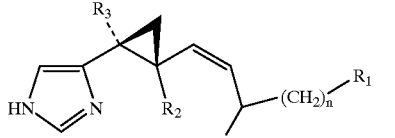
(50.0)
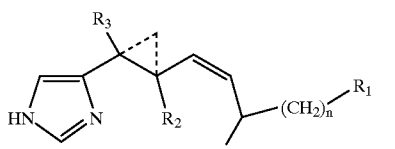
(51.0)

Particularly preferred compounds of the present invention include:

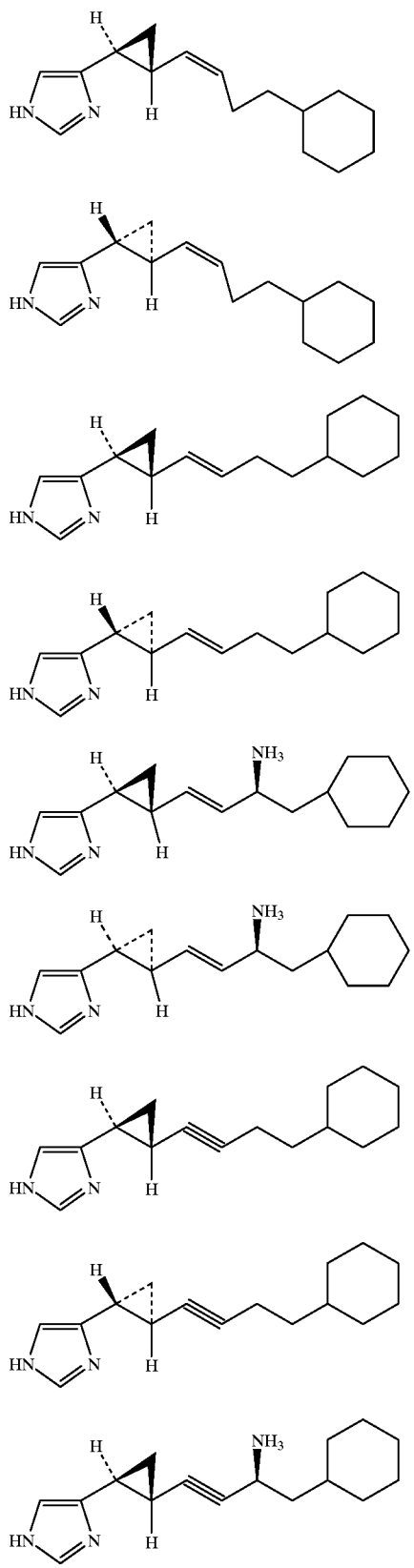

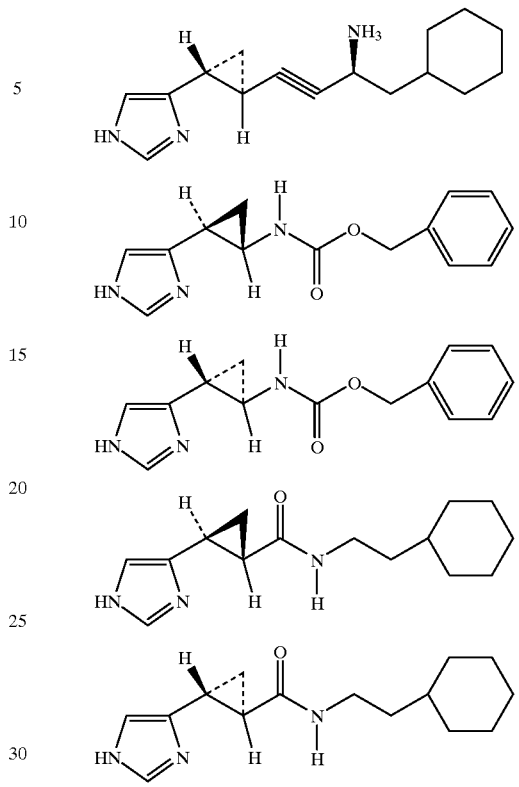

Certain compounds of the invention may exist in different isomeric (e.g., enantiomers and diastereoisomers) forms. The invention contemplates all such isomers both in pure form and in admixture, including racemic mixtures. Enol forms are also included.

The compounds of formula (1.0) can exist in unhydrated as well as hydrated forms, e.g., hemi-hydrate, mono-, tetra-, decahydrates, etc. The water may be removed by heating or other means to form the anhydrous compound. In general, the hydrated forms, with pharmaceutically acceptable solvents such as water, ethanol, and the like are equivalent to the unhydrated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such a dilute aqueous hydroxide, potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention (See, for example, S. M. Berg, et al., "Pharmaceutical Salts," *J. Pharm. Sci.,* 6-6: 1–19 (1997) which is incorporated herein by reference.

As throughout this specification and appended claims, the following terms have the meanings ascribed to them:

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "heterocyclic" as used herein refers to a closed-ring structure in which one or more of the atoms in the ring is an element other than carbon. Representative heterocyclic groups are preferably saturated and include pyrrolidines, tetrahydrofuranes, tetrahydrothiophenes, tetrahydroisoquinolines and octahydroindole groups.

The term "substituted phenyl" as used herein refers to a phenyl group substituted by one or more groups such as alkyl, halogen, amino, methoxy, and cyano groups.

The term "bicyclic alkyl" as used herein refers to an organic compound having two ring structures connected to an alkyl group. They may or may not be the same type of ring and the rings may be substituted by one or more groups. Representative bicyclic alkyl groups include adamanthyl, decahydronaphthalene and norbornane.

Individual enantiomeric forms of compounds of the present invention can be separated from mixtures thereof by techniques well known in the art. For example, a mixture of diastereoisomeric salts may be formed by reacting the compounds of the present invention with an optically pure form of the acid, followed by purification of the mixture of diastereoisomers by recrystallization or chromatography and subsequent recovery of the resolved compound from the salt by basification. Alternatively, the optical isomers of the compounds of the present invention can be separated from one another by chromatographic techniques employing separation on an optically active chromatographic medium.

The present invention also provides pharmaceutical compositions which comprise one or more of the compounds of formula (1.0) above formulated together with one or more nontoxic pharmaceutically acceptable carriers. The pharmaceutical compositions may be specifically formulated for oral administration in solid or liquid form, parental injection, or for rectal administration.

The pharmaceutical compositions of this invention can be administered to humans and other animals orally, rectally, parenterally, intracisternally, intravaginally, intraperitoneally, and topically in accordance with the present invention.

Pharmaceutical compositions of this invention for parenteral injection comprise pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents and emulsifying agents.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as calcium stearate, magnesium stearate, solid polyethylene glycols, sodium lauryl surface, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain pacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum methydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithin), both natural and synthetic.

Methods to form liposomes are known in the art. See, for example, Prescott, Ed., *Methods in Cell Biology,* Volume XIV, Academic Press, New York, N.Y. (1976) p.33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Ophthalmic formulations, eye ointments, powders and solutions are also contemplated as being within the scope of the invention.

The following processes and techniques may be employed to produce compounds of formula (1.0). The reactions are performed in a solvent appropriate to the reagents and materials employed and suitable for the transformation being effected. It is understood by those skilled in the art of organic synthesis that the functionality present in the molecule must be consistent with the chemical transformation proposed. This will frequently necessitate judgment as to the order of synthetic steps, protecting groups required and deprotection conditions.

A. Preparation of Compounds Wherein A is —CONH— or CON(CH$_3$)

Scheme I

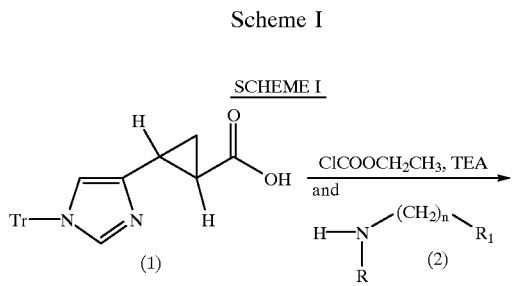

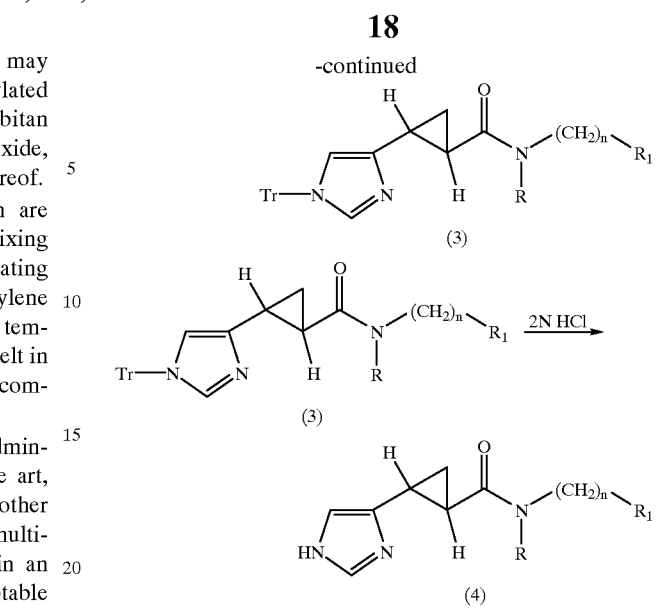

According to the foregoing reaction scheme 1,3-[1-(triphenylmethyl)-1H-imidazol-4-yl]-cyclopropanecarboxlic acid (1), prepared as a racemic mixture of trans cyclopropane using the method of Berger, et al., *J. Med. Chem.,* (1970), 1–3: 33–35, is converted to an activated ester through the action of ethyl chloroformate and triethylamine. The activated ester is reacted in situ with amine (2) to provide the 3-[1-(triphenylmethyl)-1H-imidazol-4-yl]cyclopropanecarboxamide (3). The trityl protecting group can be removed with acid, preferably aqueous 2N HCl, to give 3-[1H-imidazol-4-yl] cyclopropanecarboxamide (4).

B. Preparation of Compounds Wherein A is —CH$_2$NH— or —CH$_2$NCH$_2$—

Scheme II

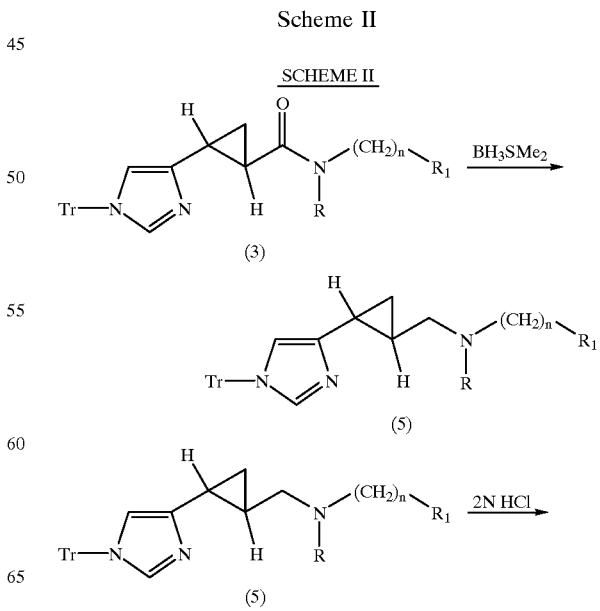

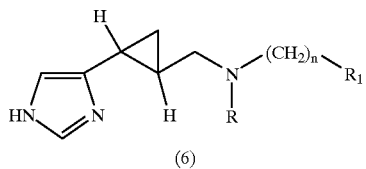

(6)

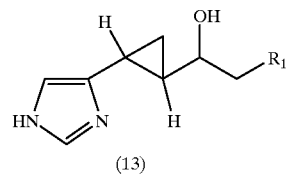

(13)

According to the foregoing reaction scheme II, 3-[1-triphenylmethyl)-1H-imidazol-4-yl]cyclopropanecarboxamide (3), prepared as described in scheme I, is treated with excess borane-methyl sulfide complex to provide 1-[1-(triphenylmethyl)-1H-imidazol-4-yl]cyclopropylamine (5). The trityl protecting group is removed with aqueous 2N HCl to give 1-[1H-imidazol-4-yl]cyclopropylamine (6).

C. Preparation of Compounds Wherein A is —CH(OH)CH$_2$

Scheme III

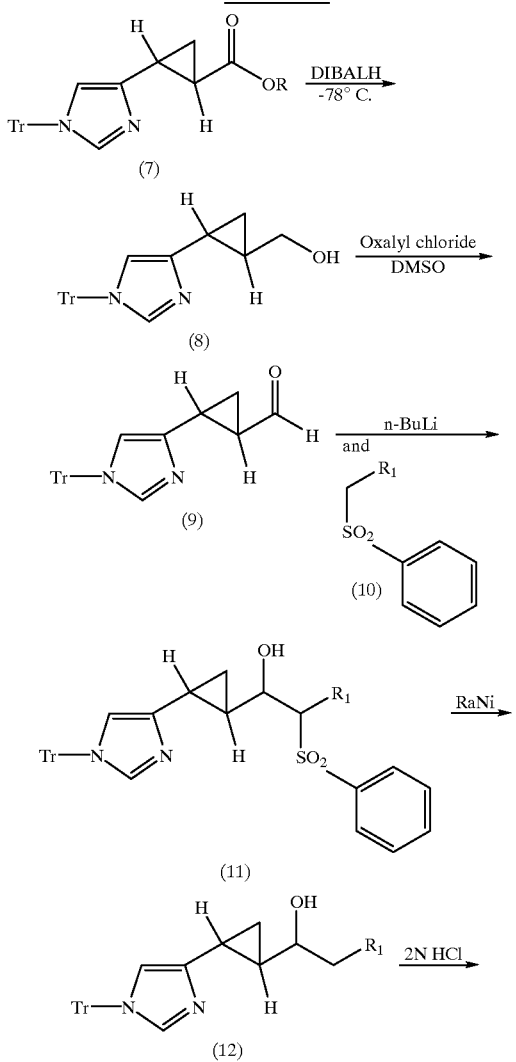

According to the foregoing reaction scheme III, 3-[1-(triphenylmethyl)-1H-imidazoL-4-yl]cyclopropanecarboxylic acid ester (7) is treated with excess DIBALH at −78° C. to provide alcohol (8). The alcohol (8) is oxidized with oxalyl chloride and DMSO to give 3-[1-(triphenylmethyl-1H-imidazoL-4yl]cyclopropylpropanal (9). The anion of sulphone (10) is prepared by the reaction of the sulphone with strong base, preferably n-BuLi, and this anion is reacted with aldehyde (9), preferably at −78° C. The diastereoisomeric mixture of beta hydroxysulphones (11) produced, is treated with excess Raney nickel (W-2) at room temperature to give a mixture of alcohols (12). The trityl protecting group can be removed, as previously described, to provide 1[1-H-imidazol-4-yl]cyclopropyl alcohols (13).

D. Preparation of Compounds Wherein A is —CH=CH— (Trans Olefins)

Scheme IV

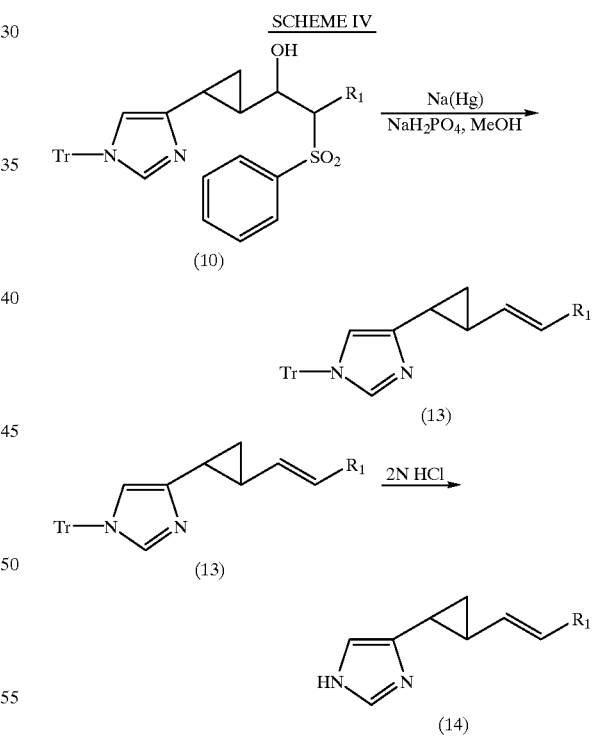

According to the foregoing reaction scheme IV, the diastereoisomeric mixture of beta hydroxy sulphones (10) synthesized as described in scheme III, is treated with excess 2–3% Na(Hg) in methanol in the presence of 4 equivalents of sodium hydrogen phosphate buffer to provide after separation of olefin isomers the 1-[1-(triphenylmethyl)-1H-imidazol-4-yl]-cyclopropyl-trans-olefin (13). Subsequent trityl deprotection gives 1-[1H-imidazoL-4-yl]cyclopropyl-trans-olefin (14).

E. Preparation of Compounds Wherein A is —CH=CH-
(Cis Olefins)

Scheme V

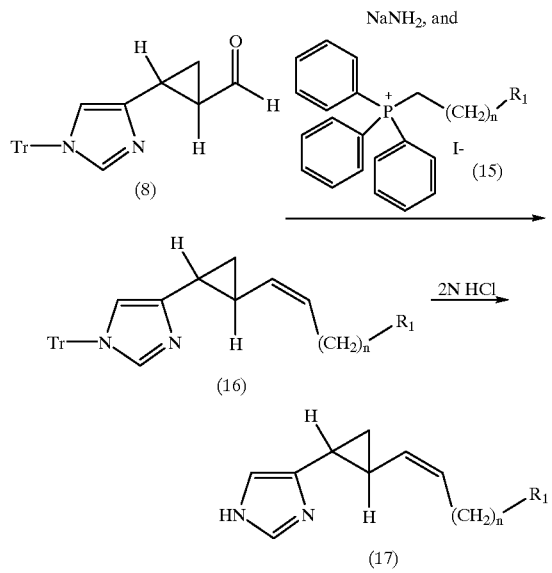

According to the foregoing reaction scheme V, 3-[1-(triphenylmethyl)-1H-imidazol-4-yl]cyclopropylpropanal (8) was converted to cis-olefin (16) via treatment with the Wittig reagent derived from treatment of the phosphonium iodide salt (15) with strong base, preferably NaNH$_2$. As before, the trityl protecting group was removed by treatment with aqueous 2N HCl to give 1-[1H-imidazol-4-yl]-cyclopropyl-cis-olefin (17).

F. Preparation of Compounds Wherein A is —COCH$_2$—

Scheme VI

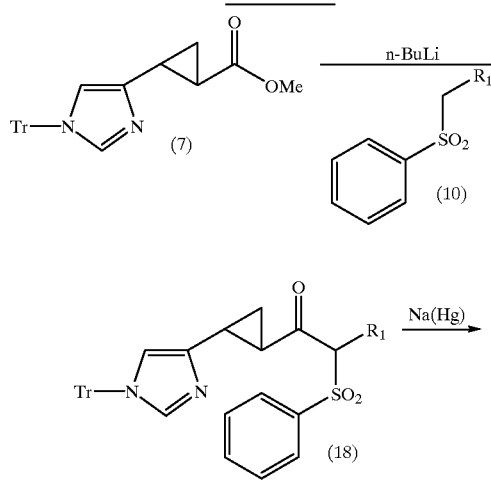

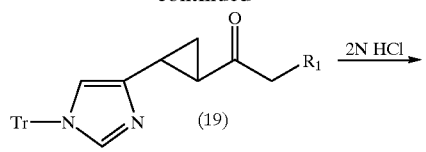

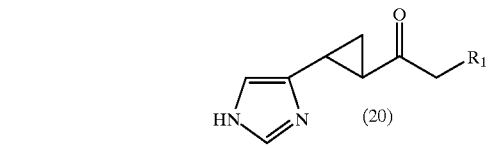

According to the foregoing reaction scheme VI, 1-[1-(triphenylmethyl)-1H-imidazol-4-yl]-cyclopropylcarboxylic ester (7) is reacted with 2.5 equivalents of the sulfone anion derived from (10) at −78° C. to give the keto-sulfone (18). Treatment with Al(Hg) or Na(Hg) provides 1-[1 -(triphenylmethyl)-1H-imidazol-4-yl]-cyclopropyl ketone (19). Trityl deprotection with 2N HCl gives 1-[1H-imidazol-4-yl]-cyclopropylketone (20).

Scheme VII

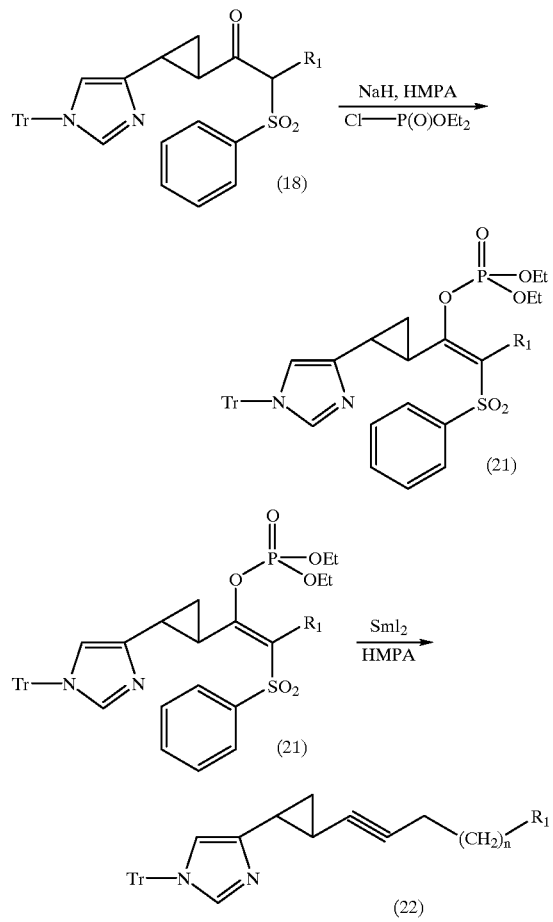

23
-continued

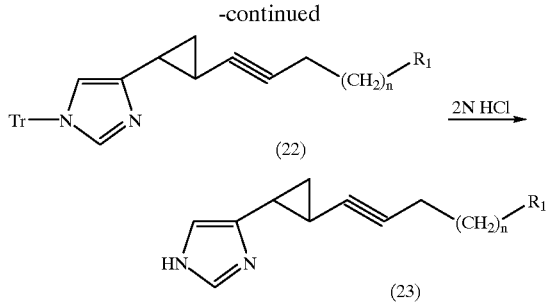

According to the foregoing reaction scheme VII, 1-[1-(triphenylmethyl)-1H-imidazol-4-yl]-cycloproply keto sulfone (18), prepared following scheme VI, is treated with NaH in the presence of HMPA, followed by diethyl phosphorochloridate to give the enol phosphate (21). Treatment of enol phosphate (21) with excess $SmI_2$ in THF/HMPA provides 1-[1H-imidazol-4-yl]-cyclopropyl acetylene (22). Finally, deprotection of the trityl protecting group with 2N HCl gives 1-[1H-imidazol-4-yl]-cyclopropyl acetylene (23).

H. Preparation of Compounds Wherein A is —$CH_2CH_2$—

Scheme VIII

SCHEME VIII

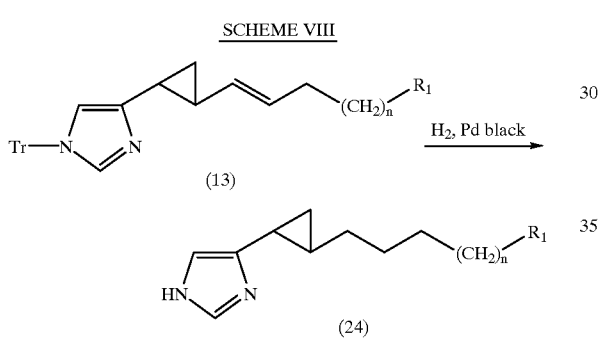

According to the foregoing reaction scheme VIII, the 1 [1-(triphenylmethyl)-1H-imidazol-4-yl]-cyclopropyl-trans-olefin (13), prepared following scheme IV, is subjected to catalytic hydrogenation under the conditions described by Zervas et al., *J. Am. Chem. Soc.*, 7–8: 1359 (1956), to reduce the carbon-carbon double bond and deprotect the trityl group, and provide the 1-[1H-imidazol-4-yl]-cyclopropane (24).

I. Preparation of Compounds Wherein A is —$CH_2O$—

Scheme IX

SCHEME IX

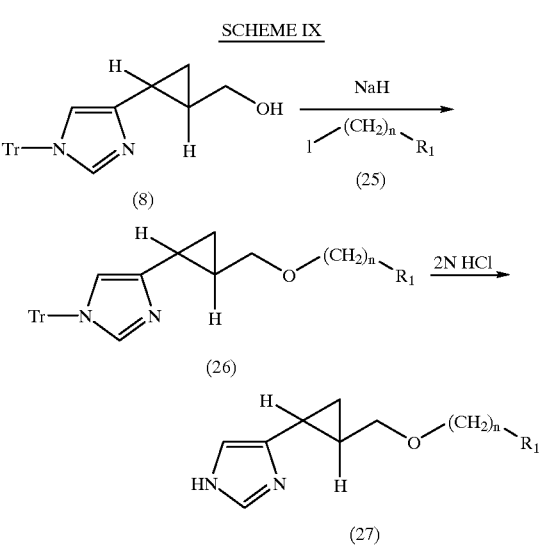

According to the foregoing reaction scheme IX, the racemic mixture of 1-[1-(triphenylmethyl)-1H-imidazoyl-4-yl]-cyclopropyl alcohols (8), prepared following the procedure outlined in scheme III, is treated with sodium hydride and reacted with iodide (25) to provide 1-[1-(triphenylmethyl)-1H-imidazoyl-4-yl]-cyclopropyl ethers (26). The trityl protecting group is removed with aqueous 2N HCl to give 1-[1H-imidazoyl-4-yl]cyclopropyl ether (27).

J. Preparation of Compounds Wherein A is —$CH_2S$—

Scheme X

SCHEME X

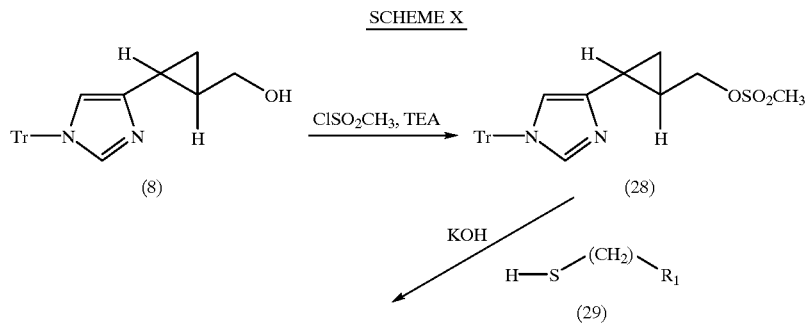

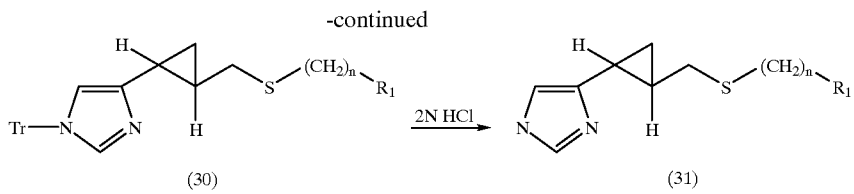

According to the foregoing reaction scheme X, the racemic mixture of 1-[1-(triphenylmethyl)-1H-imidazoyl-4-yl]-cyclopropyl alcohols (8) is treated with methanesulfonyl chloride and triethylamine to provide the corresponding mesylates (28). The mesylates (28) were treated with thiolate (29) to afford 1-[1-(triphenylmethyl)-1H-imidazoyl-4-yl]-cyclopropyl sulfides (30). The trityl protecting group is removed with aqueous 2N HCl to give 1-[1H-imidazol-4-yl]cyclopropyl sulfides(31).

K. Preparation of Compounds Wherein A is —NH—(COO)—R

Scheme XI

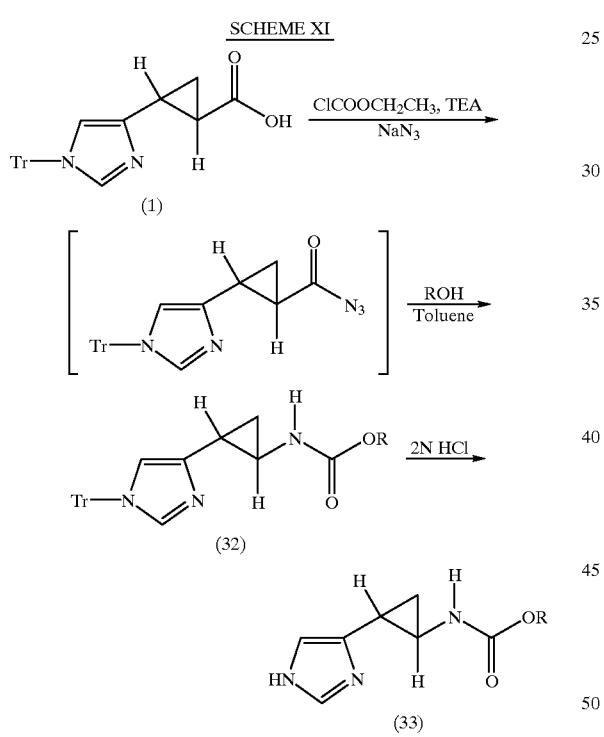

According to the foregoing reaction scheme XI, 3-[1-(triphenylmethyl)-1H-imidazoyl-4-yl] cyclopropanecarboxylic acid (1) is converted to an active ester through the action of ethyl chloroformate and triethylamine. The activated ester is reacted in situ with sodium azide to provide the acyl azide, which is heated at reflux in toluene in the presence of alcohol, to give 1-[1-(triphenylmethyl)-1H-imidazoyl-4-yl]cyclopropyl carbamate (32). Deprotection of the trityl group with 2N HCl gives 1-[1H-imidazoyl4-yl]-cyclopropyl carbamate (33).

L. Preparation of Compounds Wherein A is —NHCO— or —N(CH$_2$)CO— and X is H or NH Scheme XII

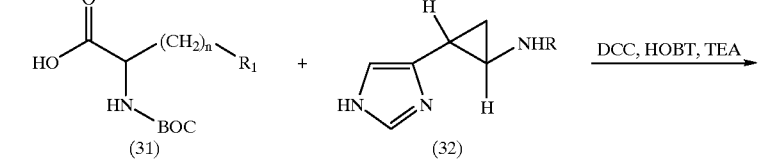

-continued

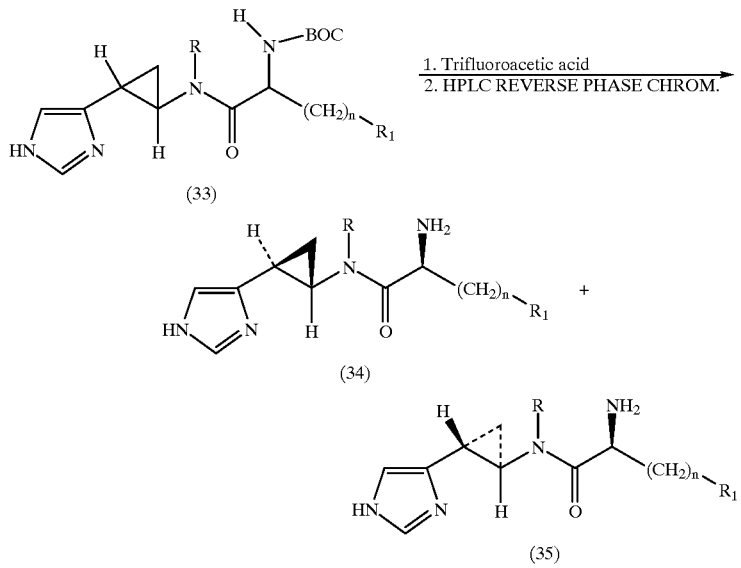

According to the foregoing reaction scheme XII, the racemic mixture of 2-[1H-imidazol-4-yl]-(1R,2R)-trans-cyclopropylamine (R=H) and 2-[1H-imidazol-4-yl]-(1S,2S)-trans-cyclopropylamine (32), prepared according to the method of Burger et al., *J. Med. Chem.,* (1970), 1–3: 33–35, is reacted with the appropriate amino acid (31), (natural L-configuration), under standard peptide coupling conditions using DCC and HOBT. After the reaction is complete (tlc or hplc analysis), the diastereomeric mixture of amides (33) is separated by reverse phase HPLC chromatography using $CH_3CN/H_2O/0.1\%$ TFA as eluent to provide pure diastereoisomers (34) and (35).

M. Preparation of Chiral Cyclopropane Compounds

Scheme XIII

Chiral cyclopropane containing compounds that are claimed as histamine $H_3$ receptor antagonists were prepared from 3-[(1-(triphenylmethyl)-1H-imidazoL-4-yl)]-(2R,3R)-trans-cyclopropanoic butyl ester (36) or 3-[(1-(triphenylmethyl)-1H-imidazol-4-yl)]-(2S,3S)-trans-cyclopropanoic butyl ester (37). The racemic mixture of these enantiomers were separated using a chiral column (Regis Serial # 0112201) and a mobile phase of 90/10 Hexane/isopropyl alcohol. Using this column, enantiomer (37) had a retention time of 7.315 minutes, and enantiomer (36) had a retention time of 5.787 minutes.

The present invention is further illustrated by the following representative examples:

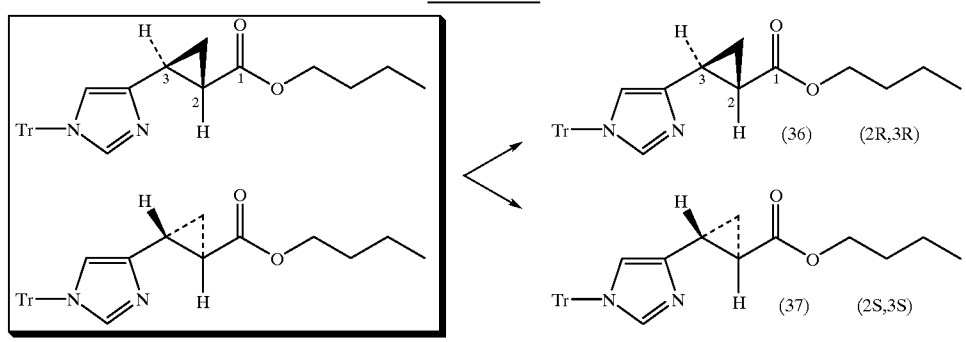

EXAMPLE 1

Preparation of racemic mixture of N-(1-Benzyl)-3-[(1H-imidazol-4-yl)]-(2R,3R)-trans-cyclopropanamide and N-(1-Benzyl)-3-[(1H-imidazol-4-yl)]-(2S,3S)-trans-cyclopropanamide hydrochloride ((±-trans-(2-imidazol-4-ylcyclopropyl-N-benzamide)

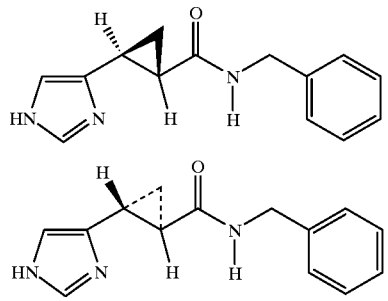

The racemic mixture of 3-[(1-(triphenylmethyl)-1H-imidazol-4-yl)]-trans-(2R,3R)-cyclopropanoic acid and 3-[(1-(triphenylmethyl)-1H-imidazol-4-yl]-trans-(2S,3S)-cyclopropanic acid, prepared according to the method of Burger, et al., *J. Med. Chem.*, (1970), 1–3: 33–35, (0.334 g, 0.84 mM) was suspended in 5 ml of distilled water. Sufficient acetone (35 ml) was added to complete solution, and the homogeneous solution was cooled to 0–5° C. Triethylamine (0.101 g., 1.0 mM) in 5 ml of acetone was added, followed by dropwise addition of ethyl chloroformate (0.108 g, 1.0 mM). The reaction mixture was stirred for 30 minutes at 0° C., and then a solution of benzylamine (0.16 g, 1.5 mM) in 10 ml of acetone was added dropwise. The reaction mixture was stirred at 0–5° C. for 1 hour, and then added to cold saturated ammonium chloride solution (100 ml), and extracted with ethyl acetate (2×100 ml). The combined ethyl acetate extracts were separated, dried over magnesium sulfate, filtered, and evaporated in vacuo to provide a crude yellow oil. The crude yellow oil was directly dissolved in 5 ml of methanol. 10 ml of 2N HCl was added, and the mixture heated at reflux for 40 minutes. The reaction mixture was cooled to room temperature, filtered, and the filtrate evaporated in vacuo to dryness. The remaining solid was triturated with 1:1 mixture of ethyl acetate/hexane (2×30 ml), collected by filtration, and dried under vacuum to give 109 mgs of racemic mixture of N-(1-benzyl)-3-[(1H-imidazol-4-yl)]-trans-(2S,3S)-cyclopropanamide and N-(1-Benzyl)-3-[(1H-imidazol-5-yl)]-2(S)-3(R)-cyclopropanamide hydrochloride (47%).

(±)-trans-(2-imidazol-4ylcyclopropyl))-N-benzamide (1) $^1$H-NMR (300 MHZ CD$_3$OD): δ 7.74 (s, 1H), 7.30 (m, 5H), 6.92 (s, 1H), 4.37 (AB q, 2H), 2.35 (m, 1H), 1.42 (m, 1H), 1.24 (m, 1H).

Mass Spectrum (DCI/NH$_3$): 242 (M+1)$^+$, MW=241.2942, C$_{14}$H$_{15}$N$_3$O$_1$.

EXAMPLE 2

Preparation of racemic mixture of N-(1-cyclohexylmethyl)-3-(1H-imidazol-4-yl)-trans-(2R,3R)-cyclopropanamide and N-1(cyclohexylmethyl)-3-(1H-imidazol-4-yl)-trans-(2S,3S)-cyclopropanamide hydrochloride((+)-trans-N-(cyclohexylmethyl)(2-imidazol-4-ylcyclopropyl)formamide)

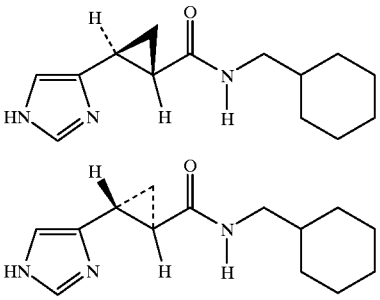

The racemic mixture of N-(1-cyclohexylmethyl)-3-(1H-imidazol-4-yl)-trans-(2R,3R)-cyclopropanamide and N-(1-cyclohexylmethyl)-3-(1H-imidazol-4-yl)-trans-(2S,3S)-cyclopropanamide hydrochloride was prepared as described in EXAMPLE 1, except cyclohexanemethyl-amine was used instead of benzylamine.

(±)-trans-N-(cyclohexylmethyl)(2-imidazol-4-ylcyclopropyl)formamide (2) $^1$H-NMR (300 MHZ, CD$_3$OD) (S, 1H), 6.92 (s,1H), 3.02 (m, 2H), 2.30 (m, 1H), 1.84 (m, 1H), 1.74 (m, 4H), 1.45 (m, 1H), 1.35 (m, 1H), 1.22 (m, 3H), 0.94 (m, 2H).

Mass Spectrum (DCI/NH$_3$): 248 (M+1)$^+$, MW=247.3422, C$_{14}$H$_{21}$N$_3$O$_1$.

EXAMPLE 3

Preparation of racemic mixture of N-[1-(3-Aminopropyl-2-pipecoline]-3-(1H-imidazol-4-yl)-trans-(2R,3R)cyclopropanamide and N-[1-(3-Aminopropyl)-2-pipecoline]-3-(1H-imidazol-4-yl)-trans-(2S,3S)-cyclopropanamide hydrochloride

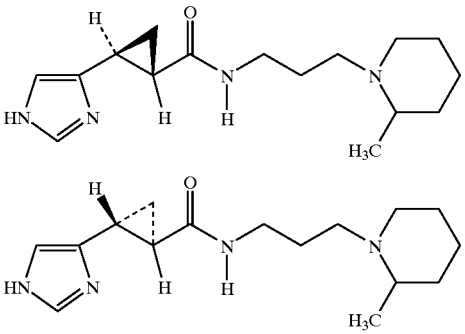

The racemic mixture of N-[1-(3-Aminopropyl-2-pipecoline]-3-(1H-imidazol-4-yl)-trans-(2R,3R) cyclopropanamide and N-[1-(3-Aminopropyl)-2-pipecoline]-3-(1H-imidazol-4-yl)-trans-(2S,3S)-cyclopropanamide hydrochloride was prepared as described in EXAMPLE 1, except 1-(3-Aminopropyl)-2-pipecoline was used instead of benzylamine.

(±)-trans-(2-imidazol-4-ylcyclopropyl)-N-(3-((±)-2-methylpiperidyl)formamide (3) $^1$H-NMR (300 MHz, CD$_3$OD): δ 8.80 (s, 1H0, 7.38 (s, 1H), 3.55 (m, 1H), 3.3 (m, 3H), 3.1 (m, 3H), 2.4 (m, 1H), 1.96 (m, 4H), 1.8 (m, 2H), 1.55 (m, 2H), 1.55 (m, 2H), 1.39 (d, 3H, J=6 Hz), 1.35 (m, 4H).

Mass Spectrum (DCI/NH$_3$): 291 (M+1)$^+$, MW=290.4109, C$_{16}$H$_{26}$N$_4$O$_1$.

EXAMPLE 4

Preparation of racemic mixture of N-[4-(3-Aminopropyl)morpholine]-3-(1H-imidazol-4-yl)-trans-(2R,3R)-cyclopropanamide and N-[4-(3-Aminopropyl)morpholine]-3-(1H-imidazol-4-yl)-trans-(2S,3S)-cyclopropanamide hydrochloride ((±)-trans-(2-imidazol-4-ylcyclopropyl)-N-(3-morpholin-4-ylpropyl)formamide)

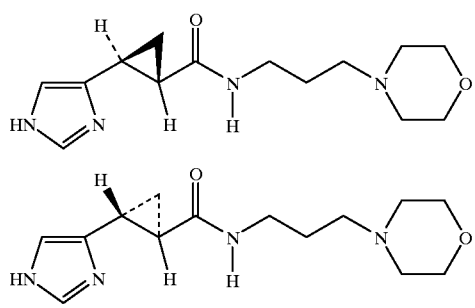

4

The racemic mixture of N-[4-(3-Aminopropyl) morpholine]-3-(1H-imidazol-4-yl)-trans-(2R,3R) cyclopropanamide and N-[4-(3-Aminopropyl)morpholine]-3-(1H-imidazol-4-yl)-trans-(2S,3S)-cyclopropanamide hydrochloride was prepared as described in EXAMPLE 1, except 4-(3-Aminopropyl)morpholine was used instead of benzylamine.

(±)-trans-(2-imidazol-4-ylcyclopropyl)-N-(3-morpholin-4-ylpropyl)formamide (4) $^1$H-NMR (300) MHZ, CD$_3$OD); δ 8.80 (s, 1H), 7.38 (s, 1H), 4.05 (m, 2H), 3.80 (m, 2H), 3.50 (m, 2H), 3.32 (m, 3H), 3.16 (m, 4H), 2.44 (m, 1H), 2.00 (m, 3H), 1.54 (m, 1H), 1.35 (m, 1H).

Mass Spectrum (DCI/NH$_3$): 279 (M+1)$^+$, MW=278.3422, C$_{14}$H$_{22}$N$_4$O$_1$.

EXAMPLE 5

Preparation of racemic mixture of N-(phenyl)-3-(1H-imidazol-4-yl)-trans-(2R,3R)-cyclopropanamide and N-(phenyl)-3-(1H-imidazol-4-yl)-trans-(2S,3S)-cyclopropanamide hydrochloride (±)-trans-N-(cyclohexylethyl)(2-imidazol-4-

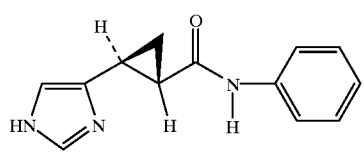

5

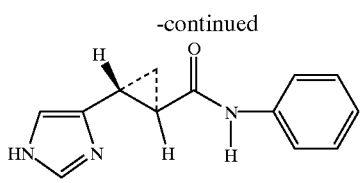

The racemic mixture of N-(phenyl)-3-(1H-imidazol-4-yl)-trans-(2R,3R)-cyclopropanamide and N-(phenyl)-3-(1H-imidazol-4-yl)-trans-(2S,3S)-cyclopropanamide hydrochloride was prepared as described in EXAMPLE 1, except aniline was used instead of benzylamine.

(±)-trans-(2-imidazol-4-ylcyclopropyl)-N-benzamide (5) $^1$H-NMR (300 MHz, CD$_3$OD): δ 7.56 (s, 1H), 7.53 (dd, 2H), 7.28 (m, 2H), 7.06 (m, 1H), 6.91 (s, 1H), 2.42 (m, 1H), 2.02 (m, 1H), 1.48 (m, 1H), 1.33 (m, 1H).

Mass Spectrum (DCI/NH$_3$): 228 (M+1)$^+$, MW=227.2672, C$_{13}$H$_{13}$N$_3$O$_1$.

EXAMPLE 6

Preparation of racemic mixture of N-[(R)-1-Cyclohexylethyl]-3-(1H-imidazol-4-yl)-trans-(2R, 3R)-cyclopropanamide and N-[(R)-1-Cyclohexylethyl]-3 -(1H-imidazol-4-yl)-trans-(2S, 3S)-cyclopropanamide hydrochloride ((±)-trans-N-(cyclohexylethyl)(2-imidazol-4-ylcycloproply) formamide)

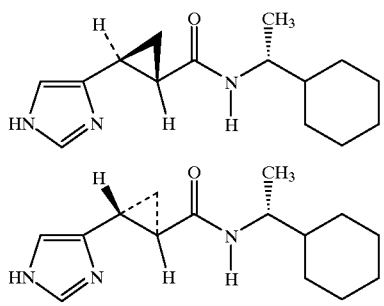

6

The racemic mixture of N-[(R)-1-Cyclohexylethyl]-4-(1H-imidazol-4-yl)-trans-(2R,3R)-cyclopropanamide and N-[(R)-1-Cyclohexylethyl]-4-(1H-imidazol-4-yl)-trans-(2S, 3S)-cyclopropanamide hydrochloride was prepared as described in EXAMPLE 1, except (R)-1-Cyclohexylethylamine was used instead of benzylamine.

(±)-trans-N-(cyclohexylethyl)(2-imidazol-4-ylcyclopropyl)formamide (6) $^1$H-NMR (300 MHz, CD$_3$OD): δ 8.78 (s, 1H), 7.36 (s, 1H), 3.73 (m, 1H), 2.41 (m, 1H), 1.97 (m, 1H), 1.74 (m, 6H), 1.50 (m, 2H), 1.40–0.91 (M, 5H), 1.09 (d, 3H).

Mass Spectrum (DCI/NH$_3$); 262 (M+1)$^+$ MW=261.343; C$_{15}$H$_{23}$N$_3$O$_1$.

EXAMPLE 7

Preparation of racemic mixture of N-[(S)-a-Cyclohexylethyl]-3-(1H-imidazol-4-yl)-trans-(2R,3R)-cyclopropanamide and N-[(S)-1-Cyclohexylethyl]-3-(1H-imidazol-4-yl)-trans-(2S,3S)-cyclopropanamide hydrochloride ((±)-trans-N-(cyclohexylethyl)(2-imidazol-4-ylcyclopropyl)formamide)

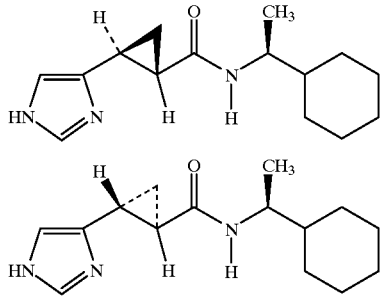

7

The racemic mixture of N-[(S)-1-Cyclohexylethyl]-3-(1H-imidazol-4-yl)-trans-(2R,3R)-cyclopropanamide and N-[(S)-1-Cyclohexylethyl]-3-(1H-imidazol-4-yl)-trans-(2S,3S)-cyclopropanamide hydrochloride was prepared as described in EXAMPLE 1, except (S)-1-Cyclohexylethylamine was used instead of benzylamine.

(±)-trans-N-(cyclohexylethyl)(2-imidazol-4-ylcyclopropyl)formamide (7) $^1$H-NMR (300 MHz, CD$_3$OD): δ 8.78 (s, 1H), 7.36 (s, 1H), 3.73 (m, 1H), 2.41 (m, 1H), 1.97 (m, 1H), 1.74 (m, 6H), 1.50 (m, 2H), 1.40–0.91 (m, 5H), 1.09 (d, 3H).

Mass Spectrum (DCI/NH$_3$): 262 (M+1)$^+$ MW=C$_{15}$H$_{23}$N$_3$O$_1$.

EXAMPLE 8

Preparation of racemic mixture of N-[1-Adamantylmethyl]-3-(1H-imidazol-4-yl)-trans-(2R,3R)-cyclopropanamide hydrochloride and N-[1-Adamantylmethyl]-3-(1H-imidazol-4-yl)-trans-(2S,3S)-cyclopropanamide ((±)-trans-N-(adamantanylmethyl)(2-imidazol-4-ylcyclopropyl)formamide

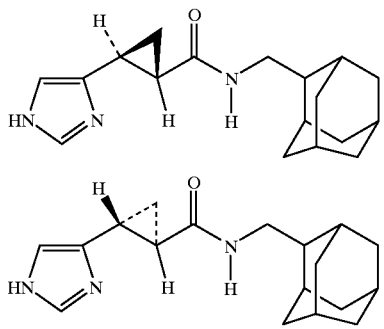

8

The racemic mixture of N-[1-Adamantylmethyl]-3-(1H-imidazol-4-yl)-trans-(2R,3R)-cyclopropanamide hydrochloride and N-[1-Adamantylmethyl]-3-(1H-imidazol-4-yl)-trans-(2S,3S)-cyclopropanamide hydrochloride was prepared as described in EXAMPLE 1, except 1-Adamantylmethylamine was used instead of benzylamine.

(±)-trans-N-adamantanylmethyl)(2-imidazol-4-ylcyclopropyl)formamide (8) $^1$H-NMR (300 MHz, CD$_3$OD): δ 8.58 (s, 1H), 6.84 (s, 1H), 3.36 (m, 1H), 2.31 (m, 1H), 2.08–1.06 (m, 14H).

Mass Spectrum (DCI/NH$_3$): 300 (M+1)$^+$ MW=C$_{18}$H$_{25}$N$_3$O$_1$.

EXAMPLE 9

Preparation of racemic mixture of N-[2-Phenylethyl]-3-(1H-imidazol-4-yl)-trans-(2R,3R)-cyclopropanamide and N-[2-Phenylethyl]-3-(1H-imidazol-4-yl)-trans-(2S,3S)-cyclopropanamide hydrochloride ((±)-trans-(2-imidazole-4-ylcyclopropyl)-N-2(2-phenylethyl)formamide)

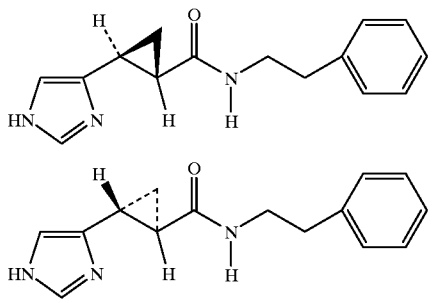

9

The racemic mixture of N-[2-Phenylethyl]-3-(1H-imidazol-4-yl)-trans-(2R,3R)-cyclopropanamide and N-[2-Phenylethyl]-3-(1H-imidazol-4-yl)-trans-(2S,3S)-cyclopropanamide hydrochloride was prepared as described in EXAMPLE 1, except 2-Phenylethylamine was used instead of benzylamine.

(±)-trans-(2-imidazol-4-ylcyclopropyl)-N-(2-phenylethyl)formamide (9) $^1$H-NMR (300 MHz, CH$_3$OD): δ 8.78 (s, 1H), 7.32 (s, 1H), 7.22 (m, 5H), 3.44 (t, 2H), 2.8 (t, 2H), 2.40 (m, 1H), 1.95 (m, 1H), 1.50 (m, 1H), 1.31 (m, 1H).

Mass Spectrum (DNI/NH$_3$): 256 (M+1)$^+$ MW=255.3211, C$_{15}$H$_{17}$N$_3$O$_1$.

EXAMPLE 10

Preparation of racemic mixture of 3-(1H-imidazol-4-yl)-trans-(2R,3R)-cyclopropyl-3'-cyclohexylpropanone and 3-(1H-imidazol-4-yl)-trans-(2S,3S)-cyclopropyl-3'-cyclohexylpropanone ((±)-trans-4-cyclohexyl-1-(2-imidazol-4-ylcyclopropyl)butan-1-one)

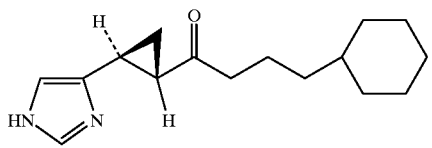

10

-continued

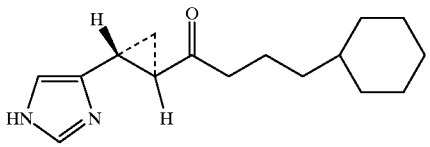

Step 1

Racemic mixture of 3-(1-Triphenylmethyl-5-imidazoyl)-2(S)-3(R)-cyclopropyl-3'-cyclohexylpropanone and 3-(1-H-imidazol-5-yl)-2(R)-3(S)-cyclopropyl-3'-cyclohexylpropanone.

To a 100 ml flask, placed under $N_2$, and charged with magnesium metal (0.076 g, 3.12 mM) and 3 ml of anhydrous ether, was added dropwise (25 min), an ether solution (15 ml) of 3-cyclohexyl-propyl iodide (0.756 g, 3.0 mM). After 3 hours at room temperature the (±)$N_1$O-(dimethyl)-3-[1-triphenylmethyl)-1H-imidazol-4-yl]-cyclopropanamide (1.22 g, 2.8 mM) in 15 ml of anhydrous THF was added dropwise to the Grignard solution at 0° C. After 1 hour at 0° C., the reaction was warmed to 50° C., and kept at that temperature for 15 hours. The reaction mixture was cooled, and quenched by the addition of saturated ammonium chloride (100 ml), and extracted (2×100 ml) with ethyl acetate. The ethyl acetate extracts were combined, dried over magnesium sulfate, filtered, and evaporated in vacuo to give a crude yellow oil. The crude oil was purified using silica gel column chromatography (ethyl acetate: hexanes, 1:1) to provide 250 mgs of racemic mixture of (±)3-[1-(triphenylmethyl)-1H-imidazol-4-yl]-cyclopropyl-3'-cyclohexylpropanone (18%).

(±)3-[1-(triphenylmethyl)-1H-imidazol-4-yl]-cyclopropyl-3'-cyclohexypropanone: $^1$H-NMR (300 MHz, $CDCL_3$): δ 7.3 (m, 12H), 7.10 (m, 4H), 6.72 (d, 1H), 2.38 (m, 3H), 1.8–1.6 (m, 2H), 1.5 (m, 9H), 1.20 (m, 7H).

Step 2

The (±)3-[1-(triphenylmethyl)-1H-imidazol-4-yl]-cyclopropyl-3'-cyclohexylpropanone (0.250 g, 0.5 mM) was heated at reflux in 10 ml of 2N HCl and 2 ml of methanol for 40 minutes. The reaction mixture was cooled, filtered, and then neutralized to pH 7 with 5% sodium hydroxide solution, dried over magnesium sulfate, filtered, and evaporated in vacuo to give a crude yellow oil. The crude oil was purified using preparative tlc with ($CHCl_3$: MeOH, 80:20) to afford 75 mgs of (±)3-[1H-imidazol-4-yl]-cyclopropyl-3'-cyclohexyl propanone (58%).

(±)-trans-4-cyclohexyl-1-(2-imidazol-4-ylcyclopropyl) butan-1-one (10) $^1$H-NMR (300 MHz, $CD_3OD$): δ 8.8 (d, 1H), 7.37 (m, 1H), 2.47 (m, 2H), 2.14 (dt, 2H), 1.69 (m, 1H), 1.55 (m, 1H), 1.44 (m, 1H), 1.32–1.10 (m, 13H), 0.87 (m, 2H).

Mass Spectrum ($DCI/NH_3$); 261 $(M+1)^+$ MW=260.3814; $C_{16}H_{24}N_2O_1$.

EXAMPLE 11

Preparation of racemic mixture of N,N-(1-Methyl, 1-Cyclohexanemethyl)-3-[1H-imidazol-4-yl]-trans-(2R,3R)-cyclopropanamide and N,N-(1-Methyl,1-Cyclohexanemethyl)-3-[1H-imidazol-4-yl]-trans-(2S,3S) ((±)-trans-N-(cyclohexylmethyl)(2-imidazol-4-ylcyclopropyl)-N-methylformamide)

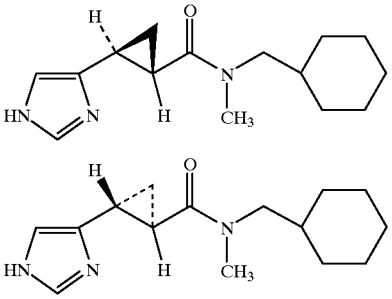

N,N-(1-Methyl,1-Cyclohexanemethyl)-3-[1H-imidazol-4-yl]-trans-(2R,3R)-cyclopropanamide and N,N-(1-Methyl, 1-Cyclohexanemethyl)-3-[1H-imidazol-4-yl]-trans-(2S,3S)-cyclopropanamide was prepared as described in EXAMPLE 1 except, N,N-(1-Methyl,1-Cyclohexanemethyl)amine was used instead of benzylamine. The intermediate, N,N-(1-Methyl,1-Cyclohexanemethyl)-3-[1H-imidazol-4-yl]-trans-(2R,3R)-cyclopropanamide and N,N-(1-Methyl,1-Cyclohexanemethyl)-3-[1-triphenylmethyl)-1H-imidazol-5-yl]-trans-(2S,3S)-cyclopropanamide was purified by silica gel column chromatography using (ethyl acetate:hexanes, 4:6). The free base of N,N-(1-Methyl,1-Cyclohexanemethyl)-3-[1H-imidazol-5-yl)]-(2R,3R)-cyclopropanamide and N,N-(1-Methyl,1-Cyclohexanemethyl)-3-[1H-imidazol-4-yl)]-(2S,3S)-cyclopropanamide hydrochloride generated in the trityl deprotection step was made by neutralizing with 5% sodium hydroxide, extracting into $CHCl_3$, drying over magnesium sulfate, filtration, and evaporation in vacuo to provide a white foam.

(±)-trans-N-(cyclohexylmethyl)(2-imidazol-4-ylcyclopropyl)-N-methylformamide (11) $^1$H-NMR (300 MHz, $CD_3OD$): δ 7.78 (s, 1H), 3.02 (m, 2H0, 2.30 (m, 1h), 2.20 (s, 3H), 1.84 (m, 1H), 1.74 (m, 4H), 1.45 (m, 1H), 1.22 (m, 3H), 0.94 (m, 2H).

Mass Spectrum ($DCI/NH_3$): 262 $(M+1)^+$, MW=261.3692, $C_{15}H_{23}N_3O_1$.

EXAMPLES 12 AND 13

Preparation of the (1R,2R)-trans-2-(S)-amino-3-cyclohenyl-N-(2-imidazol-4-ylcyclopropyl)propanamide and (1S,2S)-trans-2-(S)-amino-3-cyclohexyl-N-(2-imidazol-4-ylcyclopropyl)propanamide

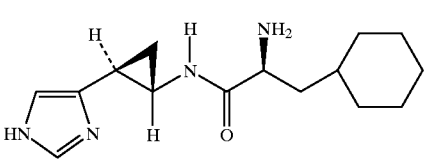

13

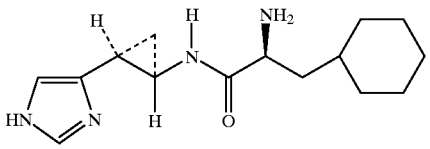

Boc-Cyclohexylalanine-Dicyclohexylamine salt (0.497 g, 1.1 mM) was added to a mixture of ethyl acetate (25 ml) and 0.5 N HCl (25 ml) for 30 minutes. The ethyl acetate layer was separated, washed with water (3×100 ml), dried over MgSO$_4$, and evaporated to give the Boc-Cyclohexylalanine free acid (1.1 mM). The acid was dissolved in 25 ml of THF and cooled to 5° C. under N$_2$. The acid was converted into a mixed anhydride by treatment with N-methyl morpholine (100 ul, 1 mM) and Isobutylchloroformate (130 ul, 1 mM). After stirring for 20 minutes, a solution of a racemic mixture of 2-(R)-3(S)-(1H-5-imidazoyl)-cyclopropylamine and 2-(S)-3(R)-(1H-5-imidazoyl)-cyclopropylamine (200 mgs, 1 mM) and triethylamine (284 u., 2 mM) in 2 ml of water was added. After 2 hours, the reaction mixture was portioned between ethyl acetate (50 ml) and water (50 ml), the ethyl acetate layer was washed with saturated sodium bicarbonate solution, water, then dried over sodium sulfate, filtered, and evaporated in vacuo to give the BOC protected amine of L-Cyclohexylalanine amide of 3(S)-(1H-5-imidazoyl)-2(R)-cyclopropylamine and its diasterisomer, the L-Cyclohexylalanine amide of 3(R)-(1H-5-imidazoyl)-2(S)-cyclopropylamine. The BOC group was deprotected by treating the crude amides directly with Trifluoroacetic acid (5 ml) for 30 minutes at r.t. The TFA was evaporated, and the residue triturated with ether to provide the ditrifluoroacetic acid salt and the diastereisomeric mixture of (1R,2R)trans-2-(S)-amino-3-(cyclohexyl-N-(2-imidazol-4-ylcyclopropyl) propanamide and (1S,2S)-trans-2-(S)-amino-3-cyclohexyl-N-(2-imidazol-4-ylcyclopropyl)propanamide (300 mgs). The diastereoisomers were separated using reverse phase HPLC.

(1R,2R)-trans-2(S)-amino-3-cyclohexyl-N-(2-imidazol-4-ylcyclopropyl)propanamide (12) $^1$H-NMR (D$_2$O, 300 MHz): d 8.44 (s, 1H), 7.18 (s, 1H), 3.88 (m, 1H), 2.87 (m, 1H), 2.09 (m, 1H), 1.6 (m, 6H), 1.27 (m, 2H), 1.1 (m, 5H), 0.88 (m, 2H).

Mass Spectrum (+FAB): [277 (M+1)$^+$, 100%] MW=276.3839, C$_{15}$H$_{24}$N$_4$O$_1$.

Analytical HPLC: CH$_3$CN/H$_2$O/0.1% TFA; Gradient: 1 n, 0%, 25 ms, 25%, 30 ms, 100%; rt. 20.07 min.

(1S,2S)-trans-2(S)-amino-3-cyclohexyl-N-(2-imidazol-4-ylcyclopropyl)propanamide (13) $^1$H-NMR (D$_2$O, 300 MHz): d 8.44 (s, 1H), 7.18 (s, 1H), 3.88 (m, 1H), 2.87 (m, 1H), 2.09 (m, 1H), 1.6 (m, 6H), 1.27 (m, 2H), 1.1 (m, 5H), 0.88 (m, 2H).

Mass Spectrum (+FAB): [277 (M+1)$^+$, 100%] MW=276.3839, C$_{15}$H$_{24}$N$_4$O$_1$.

Analytical HPLC: CH$_3$CN/H$_2$O/0.1% TFA; Gradient: 1 n, 0%, 25 ms, 25%, 30 ms, 100%; rt. 18.773 min.

EXAMPLES 14 AND 15

Preparation of the L-Octahydro-indolyl-2-carboxylic amide of 3(R)-[1H-imidazol-4-yl]-2-(R)-cyclopropamine and the L-Octahydro-indolyl-2-carboxylic amide of 3(S)-[1H-imidazol-4-yl]-2(S)-cyclopropamine. ((±)-trans-(7-azabicyclo[43.0]non-(S)-8-yl)-N-(2-imidazol-4-ylcyclopropyl) foramamide)

The preparation of the L-Octahydro-indolyl-2-carboxylic amide of 3(R)-[1H-imidazol-4yl]2(R)-cyclopropamine and the L-Octahydro-indolyl-2-carboxylic amide of 3(S)-[1H-imidazol-4-yl]-2(S)-cyclopropamine were prepared in the same way as EXAMPLES 12 and 13 except L-Octahydro-indoyl-2-carboxylic acid was used instead of L-Cyclohexylalanine.

EXAMPLE 14

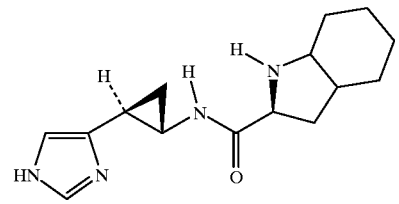

Di-Trifluoroacetic acid salt (2R,3R)-trans-(7-azabicyclo[43.0]non-(S)-8-yl)-N-(2-imidazol-4-ylcyclopropyl) formamide (14) NMR (D$_2$O, 300 MHz): d 8.4 (s, 1H), 7.06 (s, 1H), 4.25 (m, 1H), 3.65 (m, 1H), 2.8 (m, 1H), 2.30 (m, 2H), 2.2–0.90 (m, 12H).

Mass Spectrum (+FAB): [275 (M+1)$^+$, 100%] MW=274.3678, C$_{15}$H$_{22}$N$_4$O$_1$.

Analytical HPLC: CH$_3$CN/H$_2$O/0.1% TFA; Gradient: 1 nn, 0%, 20 ms, 20%, 25 ms, 100%; 30 ms, 0%; rt. 14.54 min.

EXAMPLE 15

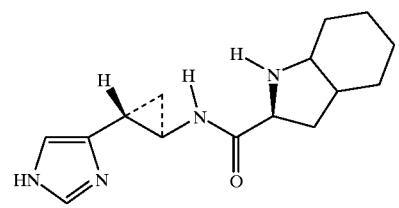

Di-Trifluoroacetic acid salt (2S,3S)-trans-(7-azabicyclo[43.0]non-(S)-8-yl-N-(2-imidazol-4-ylcyclopropyl) formamide (15) NMR (D$_2$O, 300 MHz): d 8.4 (s, 1H), 7.06 (s, 1H), 4.25 (m, 1H), 3.65 (m, 1H), 2.8 (m, 1H), 2.30 (m, 2H), 2.1–1.0 (m, 12H).

Mass Spectrum (+FAB): [275 (M+1)$^+$, 100%] MW=274.3678, C$_{15}$H$_{22}$N$_4$O$_1$.

Analytical HPLC: CH$_3$CN/H$_2$O/0.1% TFA; Gradient: 1 nn, 0%, 20 ms, 20%, 25 ms, 100%, 30 ms, 0%; rt. 16.03 min.

EXAMPLE 16

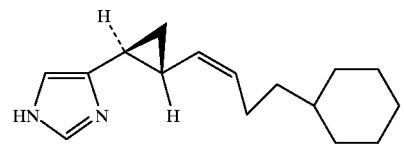

-continued

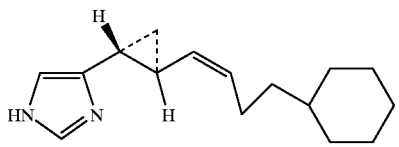

Step 1

Preparation of racemic mixture of 1(R)-[1H-imidazol-4-yl]-2(R)-cyclopropyl-6-cyclohexyl-cis-3-hexene and 1(S)-[1H-imidazol-4-yl]-2(R)-cyclopropyl-6-cyclohexyl-cis-3-hexene. ((±)-trans-4-(2-(4-cyclohexybut-cis-1-enyl) cyclopropyl)imidazole).

3-cyclohexylpropyl triphenylphosphonium iodide (1.36 g, 2.64 mM) was suspended in 100 ml of dry THF at r.t. under $N_2$. Sodium amide (0.102 g, 2.64 mM) was added, and the red-orange solution stirred to 1 hour at r.t. The solution containing the ylide derived from 3-cyclohexylpropyl triphenylphosphonium iodide was cooled to −78° C., and a THF solution (35 ml) of a racemic mixture of 3(R)-[1-(triphenylmethyl)-1H-imidazol-4-yl]-2(R)-cyclopropylcarboxaldehyde and 3(S)-[1(triphenylmethyl)-1H-imidazol-4-yl]-2(S)-cyclopropylcarboxaldehyde (1.0 g, 2.64 mM) was added slowly dropwise in 1 hour. After the addition of aldehyde was complete, the reaction was allowed to warm slowly to r.t. over a period of 5 hours. The reaction was quenched with saturated solution of ammonium chloride, and extracted with 2×150 ml of ethyl acetate. The ethyl acetate layer was separated, dried with magnesium sulfate, and evaporated in vacuo to afford the crude olefin. Purification using silica gel chomatography gave 327 mgs of racemic mixture of 1(R)-[1-(triphenylmethyl)-1H-imidazol-4-yl]-2(R)-cyclopropyl-6-cyclohexyl-cis-3-hexene and 1(S)-[1(triphenylmethyl)-1H-imidazol-4-yl]-2(S)-cyclopropyl-6-cyclohexyl-cis-3-hexene.

NMR (CDCl$_3$, 300 MHz): d 7.34–7.08 (m, 15H), 6.96 (d, 1H), 6.55 (d, 1H), 5.30 (m, 1H) 4.84 (m, 1H), 2.14 (m, 1H), 2.00 (m, 1H), 1.93 (m, 1H), 1.78–0.76 (18H).

Mass Spectrum (DCl/NH$_3$): [488 (M+1)$^+$] MW=486.7024, $C_{35}H_{38}N_2$.

Step 2

The racemic mixture of 1(R)-[1-(triphenylmethyl)-1H-imidazol-4-yl]-2(R)-cyclopropyl-6-cyclohexyl-cis-3-hexene and 1(S)-[1-(triphenylmethyl)-1H-imidazol-4-yl]-2(S)-cyclopropyl-6-cyclohexyl-cis-hexene (0.320 g, 0.657 mM) was dissolved in 10 ml of 90% acetic acid/10% water. The reaction mixture was heated at 60° C. for 2 hours. The reaction mixture was cooled, added to 50 ml of 10% sodium hydroxide solution, and extracted with chloroform (2×50 ml). The chloroform extracts were combined, dried over MgSO$_4$, and evaporated in vacuo. Purification by silica gel chromatography gave 103 mgs (viscous yellow glass) of a racemic mixture of 1(R)-[1H-imidazol-4-yl]-2(S)-cyclopropyl-6-cyclohexyl-cis-3-hexene and 1(S)-[(1H-5-imidazoyl)]-2(R)-cyclopropyl-6-cyclohexyl-cis-3-hexene (16).

(±)-trans-4-(2-(4-cyclohexylbut-cis-1-enyl)cyclopropyl) imidazole (16) NMR (CD$_3$OD, 300 MHz): d 7.6 (s, 1H), 6.82 (s, 1H), 5.34 (m, 1H), 4.90 (m, 1H), 2.18 (m, 2H), 1.90 (m, 3H), 1.60 (5H), 1.4–0.7 (m, 9H).

Mass Spectrum (DCI/NH$_3$): [245 (M+1)$^+$, 100%] MW=2.44.3814, $C_{16}H_{24}N_2$.

EXAMPLE 17

17

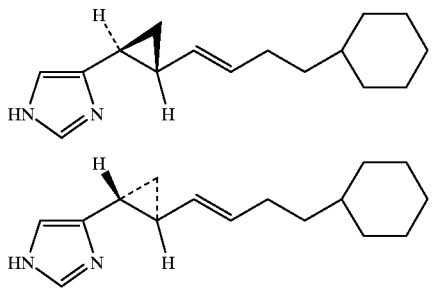

Preparation of racemic mixture of 1(R)-[1H-imidazol-4-yl]-2(R)-cyclopropyl-6-cyclohexyl-trans-3-hexene and 1(S)-[1H-imidazol-4-yl]-2(S)-cyclopropyl-6-cyclohexyl-trans-3-hexene. ((±)-trans-4-(2-(4-cyclohexylbut-trans-1-enyl) cyclopropyl)imidazole)

Step 1

3-cyclohexylpropyl phenyl sulphone (1.1 g, 4.13 mM) was dissolved in 40 ml of dry THF and cooled to −78° C. under $N_2$, n-BuLi (1.65 ml, 4.13 mM) was added dropwise, and the solution stirred for 1 hour at −78° C. A THF solution (40 ml) of a racemic mixture of 3(R)-[1-(triphenylmethyl)-1H-imidazol-4-yl]-2(R)-cyclopropylcarboxaldehyde and 3(S)-[1-(triphenylmethyl)-1H-imidazol-4-yl]-2(S)-cyclopropylcarboxaldehyde (2.56 g, 4.13 mM) was added dropwise in 15 minutes. After the addition of aldehyde was completed, the reaction was allowed to stir for 30 minutes, and then quenched with saturated ammonium chloride solution (200 ml). The reaction mixture was extracted with 2× 150 ml of ethyl acetate. The ethyl acetate layer was separated, dried with magnesium sulfate, and evaporated in vacuo to afford the crude olefin. Purification using silica gel chromatography gave 1.01 g of racemic mixture of 1(R)-[1-triphenylmethyl)-1H-imidazol-4-yl]-2(R)-cyclopropyl-3-hydroxy-4-phenylsulphone-6-cyclohexyl-hexane and 1(S)-[1-(triphenylmethyl)-1H-imidazol-4-yl]-2(S)-cyclopropyl-3-hydroxy-4-phenylsulphone-6-cyclohexyl-hexane NMR (CDCl$_3$, 300 MHz): d 7.92–7.5 (m, 5H), 7.34–7.04 (m, 15H), 6.6–6.46 (4 doublets, 2H), 3.76 (m, 0.6H), 3.67 (m, 0.5H0, 3.14 (m, 0.5H), 3.02 (m, 0.5H), 2.2–0.6 (m, 19H).

Step 2

The racemic mixture of 1(R)-[1-(triphenylmethyl)-1H-imidazol-4-yl]-2(R)-cyclopropyl-3-hydroxy-4-phenylsulphone-6-cyclohexyl-hexane and 1(S)-[1-(triphenylmethyl)-1H-imidazol-4-yl]-2(S)-cyclopropyl-3-hydroxy-4-phenylsulphone-6-cyclohexyl-hexane (0.260 g, 0.40 mM) was dissolved in 20 ml of dry dichloromethane at r.t. under $N_2$. Triethylamine (0.116 ml, 0.80 mM) was added, followed by Acetic anhydride (0.047 ml). The reaction was stirred for 5 days at r.t., water was added, and the dichloromethane layer separated, dried with magnesium sulfate, filtered, and evaporated in vacuo. Purification using silica gel column chromatography and eluting with ethyl acetate/hexanes (3:7) gave 260 mgs of (white foam) racemic mixture of 1(R)-[1-(triphenylmethyl)-1H-imidazol-4-yl]-2(R)-cyclopropyl-3-acetoxy-4-phenylsulphone-6-cyclohexyl-hexane and 1(S)-[1-(triphenylmethyl)-1H-imidazol-4-yl]-2 (S)-cyclopropyl-3-acetoxy-4-phenylsulphone-6-cyclohexyl-hexane.

NMR (CDCl₃, 300 MHz): d 7.92–7.5 (m, 5H), 7.34–7.04 (m, 15H), 6.6–6.46 (4 doublets, 2H), 5.17 (m, 0.5H), 5.04 (m, 0.5H), 3.76 (m, 0.5H), 3.02 (m, 0.5H), 2.2– 0.6 (m, 19H), 2.1 (s, 3H), CHN: $C_{43}H_{46}N_2S_1O_4$, MW=686.9144, Calc: C: 75.19, H: 6.75, N: 4.07; Found: C: 74.79, H: 6.89, N: 4.10.

Step 3

The racemic mixture of 1(R)-[1-(triphenylmethyl)-1H-imidazol-4-yl]-2(R)-cyclopropyl-3-acetoxy-4-phenylsulphone-cyclohexyl-hexane and 1(S)-[1-(triphenylmethyl)-1H-imidazol-4-yl]-2(S)-cyclopropyl-3-aceeetoxy-4-phenylsulphone-6-cyclohexyl-hexane (0.103 g, 0.15 mM) was dissolved in 8 ml of dry methanol at 0° C. under N₂. Na₂HPO₄ (0.084 g, 0.60 mM) was added, followed by 3 g of 2% CHCl₃ and water. The CHCl₃ layer was separated, dried over MgSO₄, filtered, and evaporated in vacuo. Purification using tlc afforded 52 mgs of (viscous yellow glass) racemic mixture of 1(R)-[1-(triphenylmethyl)-1H-imidazol-4-yl]-2(R)-cyclopropyl-6-cyclohexyl-trans-3-hexene and 1(S)-[1-(triphenylmethyl)-1H-imidazol-4-yl]-2(S)-cyclopropyl-6-cyclohexyl-trans-3 hexene.

NMR (CDCl₃, 300 MHz): d 7.34–7.08 (m, 15H), 6.50 (d, 1H), 6.53 (d, 1H), 5.50 (m, 0.5H), 5.30 (, 0.5H), 5.06 (m, 0.5H), 4.84 (m, 0.5H), 2.14 (m, 1H), 2.00 (m, 1H), 1.93 (m, 1H), 1.78–0.76 (18H).

Step 4

The racemic mixture of 1(R)-[1-(triphenylmethyl)-1H-imidazol-4-yl]-2(R)-cyclopropyl-6-cyclohexyl-trans-3-hexene and 1(S)-[1-(triphenylmethyl)-1H-imidazol-4-yl]-2(S)-cyclopropyl-6-cyclohexyl-trans-3 hexene (0.052 g, 0.106 mM) was heated at 80° C. in 1N HCl (6 ml) and ethanol (2 ml) for 30 minutes. The volatiles were removed by rotary evaporation, and the residue partioned between CHCl₃ (20 ml) and 10% NaOH solution. The CHCl₃ layer was separated, dried over MgSO₄, filtered, and evaporated in vacuo. Purification using tlc gave 17 mgs of racemic mixture of 1(R)-[1H-imidazol-4-yl]-2(R)-cyclopropyl-6-cyclohexyl-trans-3-hexene and 1(S)-[1-1H-imidazol-4-yl]-2(S)-cyclopropyl-6-cyclohexyl-trans-3 hexene.

(±)-trans--4-(2(4-cyclohexylbut-trans-1-enyl)cyclopyl) imidazol(17) NMR (CDCl₃, MHz): c 7.34–7.08 (m, 15H), 6.50 (d, 1H), 6.53 (d, 1H), 5.50 (m, 0.5H), 5.30 (m, 0.5H), 5.06 (m, 0.5H), 4.84 (m, 0.5H), 2.14 (m, 1H), 2.00 (m, 1H), 1.93 (m, 1H), 1.78–0.76 (18H).

Mass Spectrum (DC1/NH₃): [245 (M+1)⁺, 100%] MW=2.44.3814, $C_{16}H_{24}N_2$.

EXAMPLE 18

Preparation of racemic 3(R)-[1H-imidazol-4-yl]2 (R)-cyclopropyl-3'-cyclohexylpropyl ether and 3(S)-[1H-imidazol-4-yl]-2(S)-cyclopropyl-3'-cyclohexylpropyl ether. ((±)-trans-(3-cyclohexylpropoxy)(2-imidazol-4-ylcyclopropyl) methane)

18

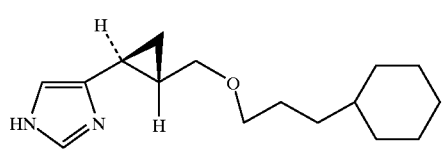

-continued

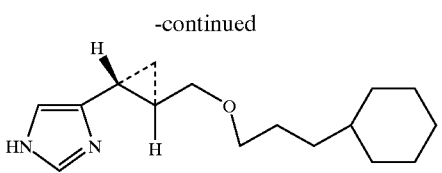

To a suspension of NaH (0.024 g, 1 mM) in 3 ml of dry DMF at 0° C. under N₂ was added a racemic mixture of 3(R)-[1-(triphenylmethyl-1H-imidazol-4-yl]-2(R)-cyclopropanol and 3(S)-[1-(triphenylmethyl-1H-imidazol-4-yl]-2(S)-cyclopropanol and (0.190 g, 0.5 mM). After stirring for 30 minutes, 3-cyclohexylpropyl iodide (0.372 g, 1.5 mM) in 1 ml of DMF was added, and the reaction stirred at 0° C. for 20 minutes. The reaction was quenched with water (20 ml), and extracted with ethyl acetate (2× 30 ml). The ethyl acetate layer was washed with brine, separated, dried over MgSO₄, filtered, and evaporated in vacuo to afford 3(R)-[1-(triphenylmethyl)-1H-imidazol-4-yl]-2(R)-cyclopropyl-3'-cyclohexylpropyl ether and 3(S)-[1-(triphenylmethyl)-1H-imidazol-4-yl]-2(S)-cyclopropyl-3'-cyclohexylpropyl ether. The trityl group was deprotected directly by treatment with 2N HCl (10 ml.) and heating at 80° C. for 30 minutes. The reaction mixture was cooled, filtered, and the filtrate evaporated in vacuo and triturated with ether to give 50 mgs of racemic mixture of 3(R)-[1H-imidazol-4-yl]-2 (R)-cyclopropyl-3'-cyclohexypropyl ether and 3(S)-[1H-imidazol-4-yl]-2(S)-cyclopropyl-3'-cyclohexypropyl ether (18).

(±)-trans--4-(3-cyclohexpropoxy)(2-imidazol-4-ylcyclopropyl)methane (18) NMR (CDCl₃, 300 MHz): d: 8.00 (d, 1H), 3.60 (M,3H), 1.72 (m, 1H), 1.48 (m, 1H), 1.58 (m, 1 1H), 1.24 (4H), 0.96 (m, 1H), 0.75 (m, 1H).

Mass Spectrum: (DCI/NH₃)[M+1, 263, 100%)] MW=262.3974: $C_{16}H_{26}O_1N_2$.

EXAMPLE 19

Preparation of racemic 1(R)-[1H-imidazol-4-yl]-2 (R)-cyclopropyl-3-hydroxy-6-cyclohexyl-hexane and 1(S)-[1H-imidazol-4-yl]-2(S)-cyclopropyl-3-hydroxy-6-cyclohexyl-hexane. ((±)-trans-4-cyclohexyl-1-(2-imidazol-4-ylcyclopropyl)butan-1-ol)

19

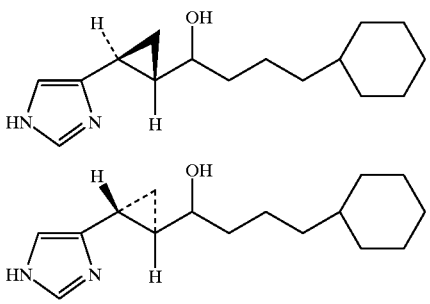

To a solution of a racemic mixture of 3-[1-(triphenylmethyl-1H-imidazol-4-yl]-2(R)-3(R)-cyclopropyl-3'-cyclohexylpropanone and 3-[1-(triphenylmethyl-1H-4-yl]-2(S)-3(S)-cyclopropyl-3'-cyclohexylpropanone (251 mg, 0.5 mM) in 15 (15 ml) of methanol cooled to −20° C. was added portionwise NaBH₄ solution (5ml). The reaction mixture was partioned between ethyl acetate and water (50/50). The ethyl acetate layer was separated, dried over MgSO$_4$, filtered, and evaporated in vacuo to give crude alcohols. The alcohols were added to 10 ml of 2N HCl and heated at 80° C. for 30 minutes. The reaction mixture was cooled, filtered and the filtrate evaporated in vacuo, the triturated with ether to give 48 mgs of racemic 1(R)-[1H-imidazol-4-yl]-2(R)-cyclopropyl-3-hydroxy-6-cyclohexyl-hexane and 1(S)-[1H-imidazol-4-yl]-2(S)-cyclopropyl-3-hydroxy-6-cyclohexyl-hexane (19).

(±)-trans-4-cyclohexyl-1-(2-imidazol-4-ylcyclopropyl (butan-1-01 (19) NMR (CD$_3$OD, 300 MHz): d 8.8 (d, 1H), 7.37 (m, 1H), 2.07 (m, 2H), 1.74 (m, 2H), 1.69 (m, 1H), 1.55 (m, 1H), 1.44 (m, 1H), 1.32–1.10 (m, 13H), 0.87 (m, 2H).

Mass Spectrum (DCI/NH$_3$): 263 (M+1)$^+$ MW=262.3974; C$_{16}$H$_{26}$N$_2$O$_1$.

EXAMPLES 20 AND 21

Preparation of 1(R)-[1H-imidazol-4-yl]-2(R)-cyclopropyl-5(S)-amino-6-cyclohexyl-3-trans-hexene and 1(R)-[1H-imidazol-4-yl]-2(R)-cyclopropyl-5(S)-amino-6-cyclohexyl-3-cis-hexene. ((1R,2R)-trans-1-cyclohexyl-4-(2-imidazol-4-ylcyclopropyl)but-3-en-2(S)-ylamine)

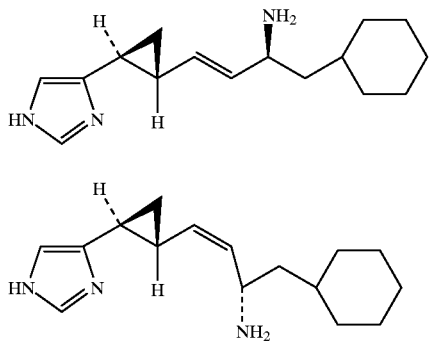

Step 1

3-cyclohexyl-1N-BOC-amino-propylphenyl sulfone (3.4 grams, 9.2 mmoles) was dissolved in 150 ml of dry THF and cooled to −78° C. under N$_2$. n-BuLi (2.5 M, 7.3 ml, 18.3 mmoles) was added dropwise via syringe, and the reaction mixture stirred at −78° C. for 1 hour. [1-(triphenylmethyl)-1H)-imidazol-4-yl]-2-cyclopropylpropanal (3.5 grams, 9.2 mmoles) was dissolved in 100 ml of dry THF and added to the THF solution of sulfone anion slowly via syringe. After the addition was complete, the reaction was stirred for 1 hour. The reaction was quenched by the addition of a saturated solution of ammonium chloride (500 ml), and extracted with ethyl acetate (2×150 ml). The ethyl acetate layer was separated dried over MgSO$_4$, filtered, and evaporated in vacuo to afford a viscous yellow oil. The crude product was purified by silica gel column chromatography using ethyl acetate/hexanes (3:7) to give 4.6 grams white solid, the racemic mixture of 1-[1-(triphenylmethyl)-1H-imidazol-4-yl]cyclopropyl-3-hydroxy-4-phenylsulfonyl-5-(N-BOC)-amino-6-cyclohexyl hexane.

Step 2

1-[1-(triphenylmethyl)-1H-imidazol-4-yl]cyclopropyl-3-hydroxy-4-phenylsulfonyl-5-(N-BOC)-amino-6-cyclohexyl hexane (4.6 grams, 6.06 mmoles) was dissolved in dry methanol. Sodium hydrogen phosphate monobasic (6.02 grams, 42.4 mmoles) was added, and the reaction was cooled to 0° C. under N$_2$. 2% Na(Hg) (2 portions of 15 grams) was added and the reaction mixture stirred for 1 hour. After that time, a second portion of Na(Hg) was added and the reaction stirred for an additional hour warming to r.t. The reaction mixture was filtered through a pad of celite, washing the pad with 100 cc of ethyl acetate. The filtrate was evaporated in vacuo, and the residue partitioned between CH$_2$Cl$_2$ and water (100:100 ml). The CH$_2$Cl$_2$ layer was separated, dried over MgSO$_4$, filtered and concentrated in vacuo to afford a yellow oil. The crude product was purified by column chromatography using ethyl acetate/hexanes (4:6) to give a white solid 1-[1-(triphenylmethyl)-1H-imidazol-4-yl]cyclopropyl-5-(N-BOC)-amino-6-cyclohexyl-3-hexene.

NMR (CDCl$_3$, 300 MHz): d: 7.30 (m, 9H), 7.12 (m, 7H), 6.58 (m, 1H), 6.53 (m, 1H), 5.40 (dd, 1H), 5.20 (m, 1H), 4.9 (m, 1H), 4.48 (m, 1H), 4.30 (m, 1H), 4.10 (m, 1H), 1.96 (m, 1H), 1.74 (m, 2H), 1.64 (m, 2H), 1.58 (s, 9H), 1.42 (s, 9H), 1.36–0.76 (m, 11H), NMR is of a 60:40 mixture of trans:cis olefins.

Step 3

1-[1-(triphenylmethyl)-1H-imidazol-4-yl]cyclopropyl-5-(N-BOC-amino-6-cyclohexyl-3-hexene (1.87 grams, 3.1 mmoles) was dissolved in 15 cc of ethanol. 50 cc of 2N HCl was added and the mixture was heated at 90° C. for 1 hour. The reaction mixture was cooled, filtered, and the filtrate neutralized with 10% NaOH solution to pH 7–8. The neutralized solution was evaporated in vacuo, and the residue partitioned between chloroform and water (100 ml each). The chloroform layer was separated, dried over sodium sulfate, filtered, and evaporated in vacuo to obtain a crude oil. The oil was purified using silica gel column chromatography using MeOH/Ethyl acetate/NH$_4$OH (9:90:1), to afford a pale yellow solid, 1(R)-[1H-imidazol-4-yl]-2(R)-cyclopropyl-5-(S)-amino-6-cyclohexyl-3-trans-hexene (20) and a yellow oil, 1(R)-[1H-imidazol-4-yl]-2(R)-cyclopropyl-5-(S)-amino-6-cyclohexyl-3-cis-hexene 21).

(1R,2R)-trans-1-cyclohexyl-4-(2-imidazol-4-ylcyclopropyl)but-trans-3-en-2(S)-ylamine (20) NMR (CDCl$_3$, 300 MHz) Trans isomer: d 7.49 (s, 1H), 6.76 (s, 1H), 5.46 (dd, 1H), 5.20 (dd, 1H), 3.33 (q, 1H), 1.82 M, 1H), 1.76–1.56 (m, 6H), 1.36–1.12 (m, 8H), 0.98–0.80 (m, 3H).

(1R,2R)-trans-1-cyclohexyl-4-ylcyclopropyl)but-trans-3-en-2(S)-ylamine (21 NMR (CDCl$_3$, 300 MHz): δ 7.49 (s, 1H), 6.76 (s, 1H), 5.21 (t, 1H), 4.94 (t, 1H),3.86 (q, 1H), 2-40–1.96 (m, 5H), 1.86 (m, 2H), 1.68 (m, 4H), 1.40–1.10 (m, 5H), 0.92 (m, 2H).

Mass Spectrum (DC1/NH$_3$): 260 (M+1)$^+$, MW=269.3835, C$_{16}$H$_{25}$N$_3$.

EXAMPLE 22

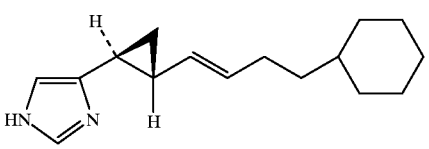

Preparation of chiral 1-(R)-[1H-imidazol-4-yl]-(2R)-cyclopropyl-6-cyclohexyl-3-trans-hexene.
((1R,2R)-trans--4-(2-(4-cyclohexylbut-trans-1-enyl) cyclopropyl)imidazole)

Chiral 1-(R)-[1H-imidazol-4-yl]-(2R)-cyclopropyl-6-cyclohexyl-3-trans-hexene was prepared using compound 36 (see Scheme XIII), 3-[1-(triphenylmethyl)-1H-imidazol-4-yl]-2(R)-3(R)-cyclopropanoic butyl ester. The procedures used were the same as described for EXAMPLE 17.

Step 1

1(S)-[1-Triphenylmethyl-5-imidazoyl]-2(R)-cyclopropyl-3-hydroxy-4-phenylsulfonyl-6-cyclohexyl hexane (a diastereomeric mixture of hydroxy sulfones) (0.85 grams, 1.32 mmoles) was dissolved in 50 cc of dry methanol at 0° C. Sodium phosphate dibasic (1.30 grams) was added, followed by 11,30 grams of 2% Na(Hg). The reaction mixture was stirred for 1 hour at 0° C. The ice bath was removed, another 10 gram portion of 2% Na(Hg) was added, and the reaction mixture stirred for 1 hour at r.t. Finally, a third portion of 10 grams of 2% Na(Hb) was added, and the reaction stirred for 2 hours. The reaction mixture was filtered through a pad of celite, washing the pad with 50 cc of methanol, followed by 50 cc of ethyl acetate. The filtrate was evaporated in vacuo, and the residue partitioned between water (100 cc) and ethyl acetate (100 cc). The ethyl acetate layer was separated, dried over MgSO$_4$, filtered and evaporated in vacuo. The crude product obtained was purified by silica gel column chromatography using ethyl acetate/hexanes (1:9) to provide 485 mgs of colorless viscous oil, a 1:1 mixture of 1(R)-[1-triphenylmethyl)-1H-imidazol-4-yl]-2(R)-cyclopropyl-6-cyclohexyl-3-trans-hexene and 1(R)-[1-(triphenylmethyl)-1H-imidazol-4-yl]-2(R)-cyclopropyl-6-cyclohexyl-3-cis-hexene.

NMR (CDCl$_3$, 300 MHz), d 7.30 (m, 9H), 7.12 (m, 7H), 6.55 (br s, 1H), 6.52 (br s, 1H), 5.5 (m, 1H), 5.3 (m, 1H), 5.06 (m, 1H), 4.84 (m, 1H), 2.14 (m, 2H), 1,96 (m, 2H), 1.68 (m, 5H), 1.16 (m, 5H), 0.82 (m, 3H), NMR is of a 1:1 cis/trans mixture of geometrical isomers.

Step 2

The 1:1 mixture of 1(R)-[1-(triphenylmethyl)-1H-imidazol-4-yl]-2(R)-cyclopropyl- 6-cyclohexyl-3-trans-hexene and 1(R)-[1-(triphenylmethyl)-1H-imidazol-4-yl]-2(R)-cyclopropyl-6-cyclohexyl-3-cis-hexene (0.475 grams) was dissolved in 3 cc of ethanol. 40 cc of 2N HCl was added, and the reaction mixture heated at 90° C. for 1 hour. The reaction mixture was cooled, filtered, and neutralized with 10% sodium hydroxide solution to pH 7. The mixture was extracted with ethyl acetate (2×100 cc), the ethyl acetate layer separated, dried over MgSO$_4$, filtered, and evaporated in vacuo to afford a yellow viscous oil. The crude product was purified by silica gel column chromatography using ethyl acetate, and provided 66 mgs (less polar fraction) of a colorless glass, 1(R)-[1H-imidazol-4-yl]-2(R)-cyclopropyl-6-cyclohexyl-3-cis-hexene and 78 mgs of 1(R)-[1H-imidazol-4-yl]-2(R)-cyclopropyl-6-cyclohexyl-3-trans-hexene.

(1R,2R)-trans--4-(2-(4-cyclohexybut-trans-1-enyl)cyclopropyl)imidazol (22) NMR (CDCl$_3$, 300 MHZ): d 7.49 (d, 1H), 6.74 (d, 1H), 5.5 (dt, 1H), 5.08 (m, 1H), 2,90 (br s, 1H), 1.98 (m, 2H), 1.79 (m, 1H), 1.65 (m, 5H), 1.18 (m, 6H), 0.84 (m, 2H).

EXAMPLE 23

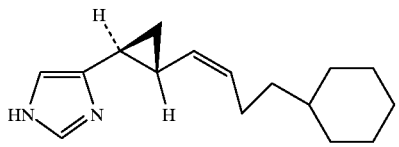

Preparation of chiral 1-(R)-[1H-imidazoyl-4-yl]-(2R)-cyclopropyl-6-cyclohexyl-3-cis-hexene ((1R, 2R)-trans-4-(2-(4-cyclohexylbut-cis-1-enyl)cyclopropyl)imidazole)

See EXAMPLE 22 for the preparation of chiral 1-(R)-[1H-imidazoyl-4-yl]-(2R)-cyclopropyl-6-cyclohexyl-3-cis-hexene.

(1R,2R)-trans-4-(2-(4-cyclohexylbut-cis-1-enyl)cyclopropyl)imidazole (23) NMR (CDCl$_3$, 30 MHZ): d 7.50 (d, 1H), 6.76 (d, 1H), 5.33 (dt, 1H), 4.86 (m, 1H), 2.90 (br s, 1H), 1.88 (m, 1H), 1.82 (m, 1H), 1.65 (m, 5H), 1.20 (m, 6H), 0.86 (m, 2H).

EXAMPLE 24

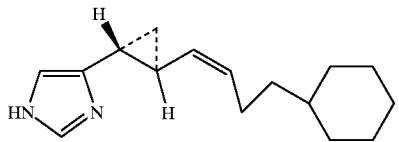

Preparation of chiral 1(S)-[1H-imidazol-4-yl]-(2S)-cyclopropyl-6-cyclohexyl-3-cis-hexene. ((1S,2S)-trans-4-(2-(4-cyclohexylbut-cis-1-enyl)cyclopropyl) imidazole Step 1

3-cyclohexylpropyl triphenylphosphonium iodide (3.6 grams, 6.9 mmoles) was suspended in 150 cc of dry THF and the mixture cooled to 0° C. under N$_2$. NaN(TMS)$_2$ (1.0M solution in THF, 6.9 cc) was added dropwise via syringe, and the reaction was allowed to stir at 0° C. for 1 hour. 3(S)-[1-Triphenylmethyl)-1H-imidazol-4-yl]-2(S)-cyclopropylpropanal (1.7 grams, 4.5 mmoles) in 50 cc of dry THF was added dropwise (0.5 hour) to the ylide solution at 0° C. The reaction was stirred for 1 hour, quenched with 200 cc of a saturated solution of ammonium chloride, and extracted with ethyl acetate (2×200 cc). The ethyl acetate layer was separated, dried over MgSO$_4$, filtered, and evaporated in vacuo to give a crude oil. The product was purified by silica gel column chromatography using CH$_2$Cl$_2$/hexanes (1:1) followed by ethyl acetate/hexanes (3:7) to give 1.33 grams of pale yellow foam, 1(S)-[1-(triphenylmethyl)-1H-imidazol-4-yl]-2(S)-cyclopropyl-6-cyclohexyl-3-cis-hexene.

NMR (CDCl$_3$, 300 MHZ): d 7.30 (m, 9H), 7.26 (d, 1H), 7.12 (m, 6H), 6.55 (d, 1H), 2.14 (m, 1H), 1.92 (m, 1H), 1.76 (m, 2H), 1.64 (m, 5H), 1.20 (m, 6H), 0.82 (m, 2H).

Step 2

1(s)-[1-Triphenylmethyl)-1H-imidazol-4-yl]-2(S)-cyclopropyl-6-cyclohexyl-3-cis-hexene (1.33 grams) was dissolved in 4 cc dry ethanol. 40 cc of 2N HCl was added, and the mixture heated at 90° C. for 1 hour. The reaction mixture was cooled, filtered, and the filtrate neutralized with 10% NaOH to pH 7. The filtrate was extracted with ethyl acetate (2×200 cc), the ethyl acetate layer separated, dried over $MgSO_4$, filtered, and evaporated in vacuo to give a yellow oil. Purification by silica gel column chromatography using ethyl acetate/hexanes (6:4) then ethyl acetate gave 488 mgs of a yellow oil, chiral 1(S)-[1-(triphenylmethyl)-1H-imidazol-4-yl]-2(S)cyclopropyl-6-cyclohexyl-3-cis-hexene.

(1S,2S)-trans-4-(2-(4-cyclohexylbut-cis-1-enyl) cyclopropyl)imidazole (24) NMR ($CDCl_3$, 300 MHZ): d 7.50 (s, 1H), 6.78 (s, 1H), 534 (dt, 1H), 4.84 (m, 1H), 2.14 (m, 2H), 1.88 (m, 1H), 1.82 (m, 1H), 1.64 (m, 5H), 1.20 (m, 7H), 0.86 (m, 3H).

EXAMPLE 25

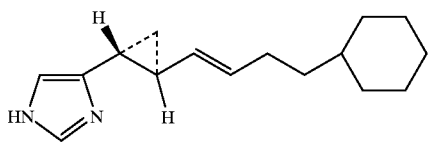

Preparation of chiral 1-(S)-[1H-imidazoyl-4-yl]-(2S)-cyclopropyl-6-cyclohexyl-3-trans-hexene. ((1S, 2S)-trans-4-(2-(4-cyclohexylbut-trans-1-enyl) cyclopropyl)imidazole Chiral 1-(S)-[1H-5-imidazoyl-4-yl]-(2S)-cyclopropyl-6-cyclohexyl-3-trans-hexene was prepared using the procedures outlined in EXAMPLE 22.

(1S,2S)-trans-4-(20(4-cyclohexylbut-trans-1-enyl) cyclopropyl)imidazole (25) NMR ($CDCl_3$, 300 MHZ): d 7.48 (s, 1H), 6.74 (s, 1H), 5.52 (dt, 1H), 5.08 (m, 1H), 1.98 (m, 2H), 1.88 (m, 1H), 1.82 (m, 5H), 1.64 (m, 5), 1.20 (m, 7H), 0.86 (m, 3H).

EXAMPLE 26

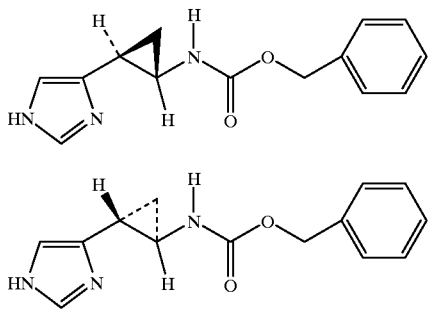

Preparation of racemic 1-(R)-[1H-imidazoyl-4-yl]-2(R)-cyclopropylamine benzyl carbonate and 1(S)-[1H-imidazol-4-yl]-2(S)-cyclopropylamine benzyl carbamate. ((±)-trans-N-(2-imidazol-4ylcyclopropyl) (phenylmethoxy)formamide)

Racemic 1-(R)-[1-(triphenylmethyl)-1H-imidazoyl-4-yl]-2(R)-cyclopropylamine benzyl carbamate and 1(S)-[1-(triphenylmethyl)-1H-imidazol-4-yl]-2(S)-cyclopropylamine benzyl carbamate were prepared as described in Scheme XI. This racemate (235 mgs) was dissolved in 1 ml of $CHCl_3$ and added to 5 ml of 2N HCl. The reaction mixture was heated at 90° C. for 45 minutes, cooled, filtered, and the filtrate concentrated in vacuo to dryness. Trituration with 2×25 ml of ethyl acetate, collection of the solid by filtration, and drying under vacuum gave 110 mgs of racemic 1-(R)-[1H-imidazoyl-4-yl]-2(R)-cyclopropylamine benzyl carbamate and 1(S)-[1H-imidazol-4-yl]-2(S)-cyclopropylamine benzyl carbamate (26).

(±)-trans-N-(2-imidazol-4ylcyclopropyl) (phenylmethoxy)formamide (26) NMR ($CD_3OD$, 300 MHZ): d 8.85 (s, 1H), 8.80 (s, 1H), 7.45 (s, 1H), 7.25 (s, 5H), 5.17 (s, 2H), 3.10 (m, 1H), 2.82 (m, 1H), 2.52 (m, 1H), 2.04 (m, 1H), 1.60 (m, 1H), 1.45 (m, 1H), 1.30 (m, 2H).

EXAMPLE 27

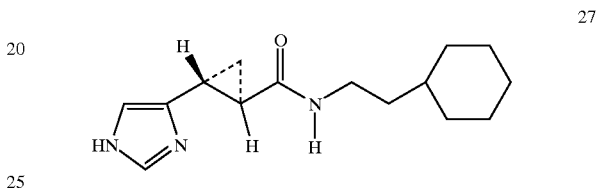

Preparation of N-[2-cyclohexylethyl]-3(S)-[1H-imidazol-4-yl]-2(S)-cyclopropanamide maleate salt. ((1S,2S)-trans-N-(2-cyclohexylethyl)(2-imidazol-4-ylcyclopropyl)formamide)

Chiral N-[2-cyclohexylethyl]-3(S)-[1H-imidazol-4-yl]-2(S)-cyclopropanamide maleate salt was made from 3-[1-(triphenylmethyl-1H-imidazol-4-yl]-2(S)-3(S)-cyclopropanoic butyl ester (37). The compound was prepared as described in EXAMPLE 1, except 2-cyclohexylethylamine was used instead of benzylamine.

(1S,2S)-trans-N(2-chclohexylethyl)(2-imidazol-4-ylcyclopropyl)formamide (27) NMR ($CD_3OD$, 300 MHZ): d 8.78 (s, 1H), 7.37 (s, 1H), 6.28 (s, 2H), 3.23 (m, 1H), 2.52 (m, 2H), 2.40 (m, 1H), 1.97 (m, 3H), 1.72 (m, 4H), 1.62–1.18 (m, 6H), 0.94 (m, 2H).

Mass Spectrum ($DCI/NH_3$): 261 $(M+1)^+$, MW=260.3612, $C_{15}H_{22}N_3O_1$.

EXAMPLE 28

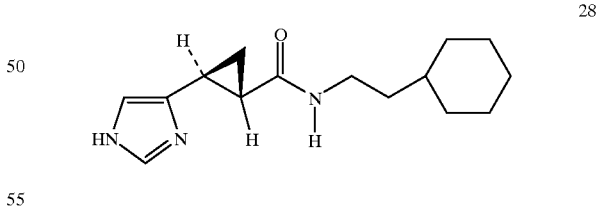

Preparation of N-[2-cyclohexylethyl]-3(R)-[1H-imidazol-4-yl]-2(R)-cyclopropanamide hydrochloride salt. ((1R,2R)-trans-N-(2-cyclohexylethyl)(2-imidazol-4-ylcyclopropyl) formamide)

Chiral N-[2-Cyclohexylethyl]-3(S)-[1H-imidazol-4-yl]-2(R)-cyclopropanamide hydrochloride salt was made from 3-[(1-(triphenylmethyl)-1H-imidazoyl-4-yl]-2(R)-3(R)-cyclopropanoic butyl ester (37). The compound was prepared as described in EXAMPLE 1, except 2-cyclohexylethylamine was used instead of benzylamine.

(1R,2R)-trans-N-(2-cyclohexylethyl)(2-imidazol-4-ylcyclopropyl)formamide (28) NMR (CD$_3$OC, 300 MHZ): d 8.78 (s, 1H), 3.23 (m, 2H), 2.52 (m, 2H), 1.96 (m, 3H), 1.72 (m, 4H), 1.56–1.18 (m, 6H), 0.94 (m, 2H).

Mass Spectrum (CD1/NH$_3$): 261 (M+1)$^+$, MW=2.60.3612, C$_{15}$,H$_{22}$,N$_3$,O$_1$.

EXAMPLE 29

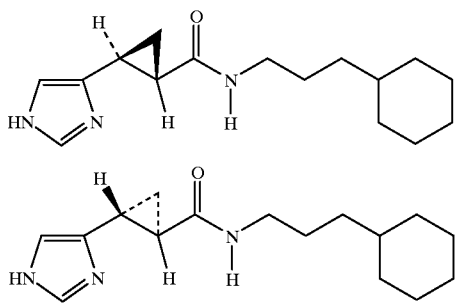

29

Preparation of racemic N-[3-cyclohexylpropyl]-3(R)-[1H-imidazoyl-4-yl]-2(R)-cyclopropanamide and N-[3-Cyclohexylpropyl]-3(S)-[1H-imidazoyl-4-yl]-2(R)-cyclopropanamide. ((±)-trans-N-(2-cyclohexylpropyl)(2-imidazol-4-ylcyclopropyl) formamide)

Racemic N-[3-cyclohexylpropyl]-3(R)-[1H-imidazoyl-4-yl]-2(R)-cyclopropanamide and N-[3-Cyclohexylpropyl]-3(S)-[1H-imidazoyl-4-yl]-2(R)-cyclopropanamide were prepared as described in EXAMPLE 1, except 3-cyclohexylpropylamine was used instead of benzylamine.

(±)-trans-N(2-cyclohexylpropyl)(2-imidazol-4-ylcyclopropyl)formamide (29) NMR (CD$_3$OD, 300 MHz): d 8.80 (d, 1H), 7.38 (d, 1H), 3.18 (m, 2H), 2.52 (m, 2H), 2.40 (m, 1H), 2.05 (m, 1H), 1.99 (m, 3H), 1.70 (m, 5H), 1.62–1.15 (m, 7H), 0.91 (m, 2H).

Mass Spectrum (DCI/NH$_3$): 276 (M+1)$^+$, MW=275.3962, C$_{16}$H$_{25}$N$_3$O$_1$.

EXAMPLE 30

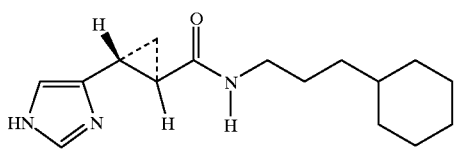

30

Preparation of chiral N-[2--cyclohexylpropyl]-3(S)-[1H-imidazol-4-yl]-2(S)-cyclopropanamide hydrochloride salt. ((1S,2S)-trans-N-(2-cyclohexylpropyl)(2-imidazol-4-ylcyclopropyl) formamide)

Chiral N-[2-cyclohexylpropyl]-3(S)-[1H-imidazol-4-yl]-2(S)-cyclopropanamide hydrochloride salt was made from 3-[1-(triphenylmethyl)-1H-imidazol-4-yl]-2(S)-3(S)-cyclopropanoic butyl ester (36), and was prepared as described in Example 1, except 3-cyclohexylpropylamine was used instead of benzylamine.

(1S,2S)-trans-N-(2-cyclohexypropyl)(2-imidazol-4-ylcyclopropyl)formamide (30) NMR (CD$_3$OD, 300 MHZ):d 8.74 (s, 1H), 7.30 (s, 1H), 3.16 (m, 2H), 2.40 (m, 1H), 1.92 (m, 1H), 1.70 (m, 6H), 1.55 (m, 7H), 0.91 (m, 2H).

Mass Spectrum (DC1/NH$_3$): 276 (M+1)$^+$, MW=275.3962, C$_{16}$H$_{25}$N$_3$O$_1$.

EXAMPLE 31

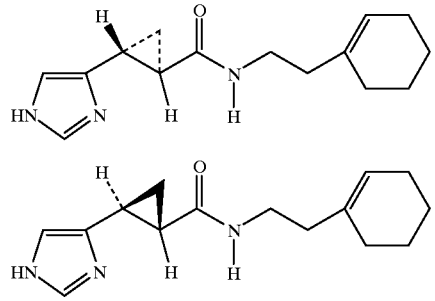

31

Preparation of racemic N-[2-cyclohex-1-enyl-ethyl]-3(R)-[1H-imidazol-4-yl]-2-(R)-cyclopropanamide HCl salt and N-[2-Cyclohex-1-enyl-ethyl]-3(S)-[1H-imidazol-4-yl]-2(S)-cyclopropanamide HCl salt. ((±)-trans-N-(2-cycloenylethyl)(2-imidazol-4-ylcyclopropyl)formamide)

Racemic N-[2-Cyclohex-1-enyl-ethyl]-3(R)-[1H-imidazol-4-yl]-2(R)-cyclopropanamide HCl salt and N-[2-Cyclohex-1-enyl-ethyl]-3(S)-[1H-imidazol-4-yl]-2(S)-cyclopropanamide HCl salt were prepared as described in Example 1, except 2-cyclohex-1-enyl-ethylamine was used instead of benzylamine.

(±)-trans-N-(2-cyclo-enylethyl)(2-imidazol-4-ylcyclopropyl)formamide (31) NMR (CD$_3$OD, 300 MHz): d 8.9 (s, 1H), 7.55 (s, 1H), 5.60 (m, 1H), 3.70 (m, 2H), 3.0 (m, 4H), 2.30 (m, 1H), 1.95 (m, 3H), 1.60 (m, 7H).

Mass Spectrum (DC1/NH$_3$): 260 (M+1)$^+$, MW=259.3532, C$_{15}$H$_{21}$N$_3$O$_1$.

EXAMPLE 32

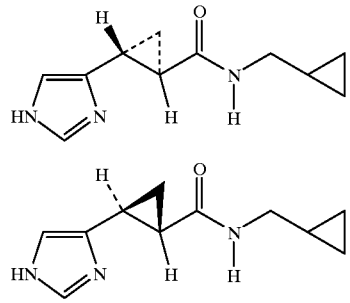

32

Preparation of racemic N-[1-cyclopropylmethyl]-3(R)-[1H-imidazol-4-yl]-2(R)-cyclopropanamide HCl salt and N-[1-cyclopropylmethyl-3(S)-[1H-imidazol-4-yl]-2(S)-cyclopropanamide HCl salt. (±)-trans-N-(cyclopropylmethyl)(2-imidazol-4-ylcyclopropyl)formamide)

Racemic N-[1-cyclopropylmethyl]-3(R)-[1H-imidazol-4-yl]-2(R)-cyclopropanamide HCl salt and N-[1- cyclopropylmethyl]-3(S)-[1H-imidazol-4-yl]-2(S)-cyclopropanamide HCl salt were prepared as described in Example 1, except (aminomethyl)cyclopropane was used instead of benzylamine.

(±)-trans-N-(cyclopropylmethyl)(2-imidazol-4-ylcyclopropyl)for-amide (32) NMR (CD$_3$OD, 300 MHz): d 8.80 (s, 1H), 7.38 (s, 1H), 3.0 (d, 1H), 2.80 (d, 1H), 2.40 (m, 1H), 1.98 (m, 1H), 1.50 (m, 1H), 1.32 (m, 1H), 0.98 (m, 1H), 0.50 (m, 2H), 0.20 (M, 2H).

Mass Spectrum (CD1/NH$_3$): 206 (M+1)$^+$, MW=2.05.2612, C$_{11}$H$_{15}$N$_3$O$_1$.

EXAMPLE 33

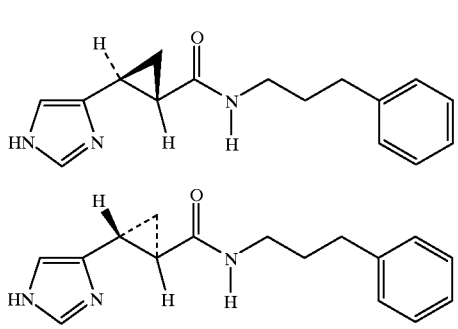

Preparation of racemic N-[3-Phenylpropyl]-3(R)-[1H-imidazol-4-yl]-2(R)-cyclopropanamide HCl salt and N-[3-Phenylpropyl-3(S)-[1H-imidazol-4-yl]-2(S)-cyclopropanamide HCl salt Racemic N-[3-Phenylpropyl]-3(R)-[1H-5-imidazoyl]-2(S)-cyclopropanamide HCl salt and N-[3-Phenylpropyl-3(S)-[1H-5-imidazoyl-2(R)-cyclopropanamide HCl salt were prepared as described in Example 1, except 3-Phenylpropylamine was used instead of benzylamine.

(±)-trans-(2-imidazol-4-ylcyclopropyl)-N-(3-phenylpropyl)formamide (33) NMR (CD$_3$OC, 300 MHz): d 8.78 (d, 1H), 7.34 (d, 1H), 7.22 (m, 5H), 3.22 (t, 2H), 2.92 (t, 1H), 2.72 (t, 2H), 2.64 (t, 2H), 2.40 (m, 1H), 1.96 (m, 1H), 1.83 (m, 1H), 1.52 (m, 1H), 1.33 (m, 1H).

Mass Spectrum (DC1/NH$_3$): 270 (M+1)$^+$, MW=269.3438, C$_{16}$H$_{19}$N$_2$O$_1$.

EXAMPLE 34

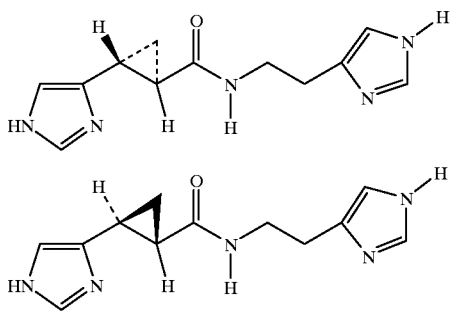

Preparation of racemic N-[2-(4)-imidazoylethyl]-3(R)-[1H-imidazol-4-yl-2(R)-cyclopropanamide HCl salt and N-[2-(4)--imidazoylethyl]-3(S)-[1H-imidazol-4-yl-2(S)-cyclopropanamide HCl salt Racemic N-[2-(4)-imidazoylethyl]-3(R)-[1H-5-imidazoyl]-2(S)-cyclopropanamide HCl salt and N-[2-(4)-imidazoylethyl]-3(S)-[1H-5-imidazoyl]-2(R)-cyclopropanamide HCl salt were prepared as described in Example 1, except N-[2-(4)-imidazoylethyl]amine was used instead of benzylamine.

(±)-trans-(2-imidazol-4-ylcyclopropyl)-N-(2-imidazol-4-ylethyl)formamide (34) NMR (CD$_3$OC, 300 MHz): d 8.82 (s, 1H), 8.79 (s, 1H), 7.36 (s, 1H), 3.54 (m, 2H), 3.30 (m, 1H), 2.94 (m, 1H), 2.40 (M, 1H), 2.02 (m, 1H), 1.48 (m, 1H), 1.32 (m, 1H).

EXAMPLE 35

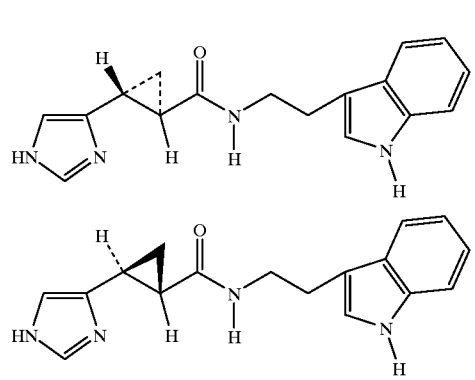

Preparation of racemic N-[3-(2-aminoethyl)indole]-3(R)-[1H-imidazol-4-yl]-2(R)-cyclopropanamide and N-[3-(2-aminoethyl)indole]-3(S)-[1H-imidazol-4-yl]-2(S)-cyclopropanamide. ((±)-trans-(2-imidazol-4-ylcyclopropyl)-N-(2-indol-3-ylethyl)formamide)

Racemic N-[3-(2-aminoethyl)indole]-3(R)-[1H-imidazol-4-yl]-2(R)-cyclopropanamide HCl salt and N-[3-(2-aminoethyl)indole]-3(S)-[1H-imidazol-4-yl]-2(S)-cyclopropanamide HCl salt were prepared as described in Example 1, except N-[3-(2-aminoethyl)indole] was used instead of benzylamine.

(±)-trans-(2-imidazol-4-ylcyclopropyl)-N-(2-indol-3-ylethyl)formamide (35) NMR (CD$_3$OD, 300 MHz): d 7.55 (d, 1H), 7.52 (s, 1H), 7.31 (d, 1H), 7.06 (m, 2H), 6.69 (m, 1H), 6.84 (s, 1H), 3.48 (m, 2H), 3.30 (m, 2H), 2.95 (m, 2H), 2.32 (m, 1H), 1.80 (m, 1H), 1.38 (m, 1H), 1.20 (m, 1H).

EXAMPLE 36

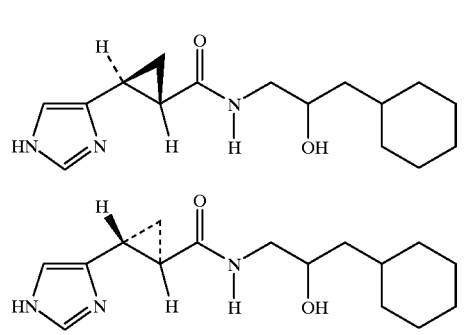

Preparation of racemic N-[3-Cyclohexyl-2-hydroxy-propyl]-3-(R)-[1H-imidazol-4-yl]-2(R)-cyclopropanamide and N-[3-Cyclohexyl-2-hydroxy-propyl]-3(S)-[1H-imidazol-4-yl]-2(S)-cyclopropanamide. ((±)-trans-N-(3-cyclohexyl-2-(±)-hydroxypropyl3(2-imidazol-4-ylcyclopropyl)formamide)

Racemic N[-3-Cyclohexyl-2-hydroxy-propyl]-3(R)-[1H-imidazol-4-yl]-2(R)-cyclopropanamide and N-[3-Cyclohexyl-2-hydroxy-propyl]-3(S)-[1H-imidazol-4-yl]-2(S)-cyclopropanamide were prepared as described in Example 1, except 3-cyclohexyl-2-hydroxy-propylamine was used instead of benzylamine.

(±)-trans-N-(3-cyclohexyl-2-(±)-hydroxypropyl)(2-imidazol-4-ylcyclopropyl)formamide (36) NMR CD$_3$OD, 300 MHz): d 8.80 (d, 1H), 7.38 (d, 1H), 4.46 (d, 1H), 4.42 (d, 1H), 4.18 (d, 1H), 4.12 (d, 1H), 4.02 (m, 1H), 3.76 (d, 1H), 3.72 (d, 1H), 3.60 (m, 1H), 3.52 (m, 1H), 3.47 (t, 2H), 2.60 (m, 1H), 2.50 (m, 1H), 2.20 (m, 1H), 1.96 (m, 1H), 1.70 (m, 5H), 1.62–1.15 (m, 7H), 0.91 (m, 2H).

EXAMPLE 37

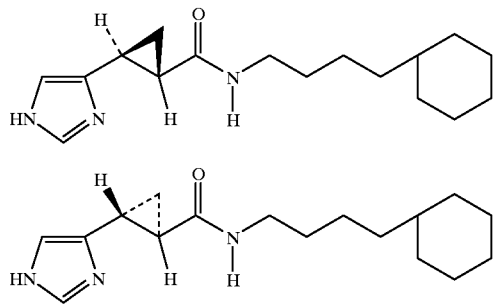

Preparation of racemic N-[4-Cyclohexylbutyl]-3(R)-[1H-imidazol-4-yl]-2(R)-cyclopropanamide and N-[4-Cyclohexylbutyl]-3(S)-[1H-imidazol-4-yl]-2(S)-cyclopropanamide. ((±)-trans-N-(4-cyclohexylbutyl)(2-imidazol-4-ylcyclopropyl)formamide)

Racemic N-[4-Cyclohexylbutyl]-3(R)-[1H-imidazol-4-yl]2(R)-cyclopropanamide and N-[4-(Cyclohexylbutyl]-3(S)-[1H-imidazol-4-yl]-2(S)-cyclopropanamide were prepared as described in Example 1, except 4-Cyclohexylbutylamine was used instead of benzylamine.

(±)-trans-N-(4-cyclohexylbutyl)(2-imidazol-4-ylcyclopropyl)formamide (37) NMR (CD$_3$Cl, 300 MHz): d 8.00 (s, 1H), 6.62 (s, 1H), 5.65 (m, 1H), 3.44 (m, 1H), 3.22 (m, 1H), 2.68 (t, 1H), 2.30 (m, 1H), 2.0 (m, 1H), 1.78 (m, 2H), 1.66 (m, 4H), 1.42 (m, 2H), 1.20 (m, 6H), 0.82 (m, 2H).

The compounds of this invention are antagonists of the histamine H$_3$ receptor. The binding affinity of the compounds of the invention to the H$_3$ receptor may be demonstrated by the procedure described below:

In Vitro Histamine H$_3$ Receptor Binding Analysis

Histamine H$_3$ receptor affinity was determined in rat cortical membranes using the H$_3$ selective agonist ligand, [$^3$H]-N$^\alpha$-methylhistamine (78.9 Ci/mole, DuPont NEN Research Products, Boston, Mass.) according to the method of West et al., (1990) Mol. Pharmacol. 38: 610–613 with modifications. Briefly, animals were sacrificed by decapitation and the cerebral cortex was rapidly removed. Rat cortices were mechanically homogenized with an Omni 1000 motor driven homogenizer in 10 volumes (wt/vol) of Krebs-Ringers Hepes buffer (pH 7.4) containing the following protease inhibitors: EDTA (10 mM), PMSF (0.1 mM), chymostatin (0.2 mg/50 mL) and leupeptin (0.2 mg/50 mL). The homogenate was centrifuged in a Sorvall at ~40,000×g for 30 min. The pellet was resuspended by mechanical homogenization in 25 mL water and lysed on ice for 30 min. The homogenate was recentrifuged and the membrane lysis was repeated. The membranes were recentrifuged and the final pellet was resuspended in 14 volumes of water to give approximately 200 μg protein/100 μl final concentration. The suspension was stored at –80° prior to use. Protein concentrations were determined by Coomassie Plus Protein Assay (Pierce, Rockford, Ill.).

The binding assay was carried out in polypropylene tubes in a total volume of 0.4 ml of 50 mM Na$^+$ Phosphate buffer (pH 7.4), containing 150–200 μg of tissue protein, 0.8–1.2 nM [$^3$H]-N$^\alpha$-methylhistamine and 0.3 to 10,000 nM GT-2016. Nonspecific binding (NSB) was accounted for by the inclusion of thioperamide (10 μM). Samples were incubated for 40 minutes at 25° C. The samples were filtered through glass fiber strips, pre-washed with 0.3% polyethyleneimine, using a Brandell cell harvester. The filters were rapidly washed three times with 4 ml of 25 mm Tris buffer containing 145 mM NaCl (pH 7.4, 4° C.). Filters were transferred to polyethylene mini-vials and counted in 3.5 ml of scintillation fluid (Ecolume, ICN Biomedicals, Inc.). Using this procedure, the non-specific binding was less than 10% of the total binding and the binding to the glass fiber filters was negligible. Saturation and competition experiments were analyzed with the ReceptorFit saturation and competition curve fitting programs (Lundon Software, Ind., Cleveland, Ohio). K's were determined using the equation K$_i$=IC$_{50}$/(1+([Ligand]/[K$_d$]). The results are given in Table 1.

TABLE 1

Histamine H$_3$ Receptor Binding Affinities

| Compound | Structure | | H$_3$ Receptor K$_i$(nM) |
|---|---|---|---|
| Example 1 | | | 53 ± 2 |

TABLE 1-continued

Histamine H₃ Receptor Binding Affinities

| Compound | Structure | H₃ Receptor $K_i$(nM) |
|---|---|---|
| Example 2 | 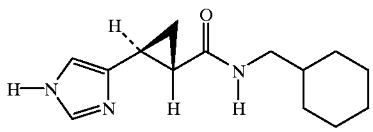 | 37 ± 4 |
| Example 2a | 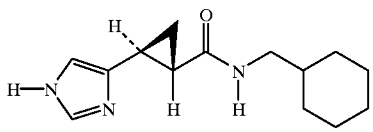 | 23 ± 1 |
| Example 2b | 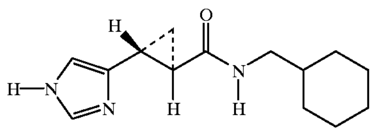 | 176 ± 9 |
| Example 3 | 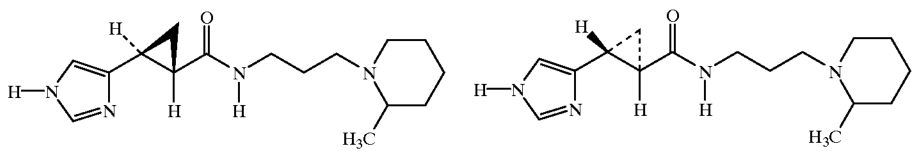 | 659 ± 52 |
| Example 4 | 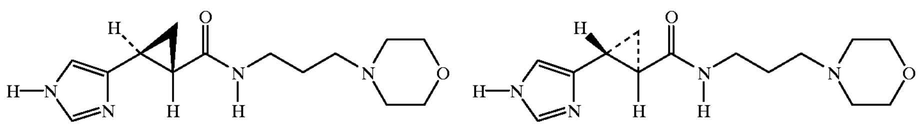 | 1402 ± 158 |
| Example 5 | 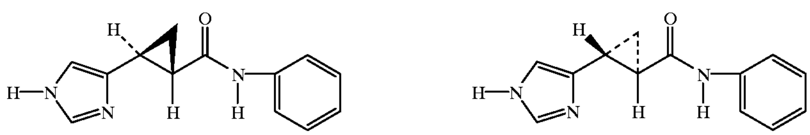 | 267 ± 26 |
| Example 6 | 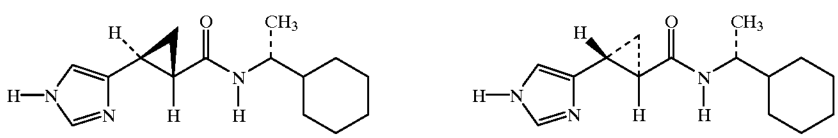 | 70 ± 8.6 |
| Example 7 | 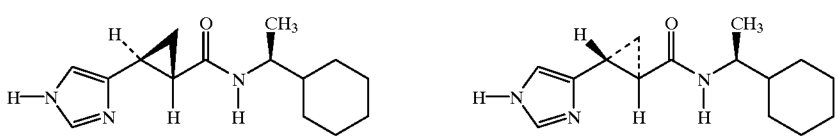 | 146 ± 13 |
| Example 8 | 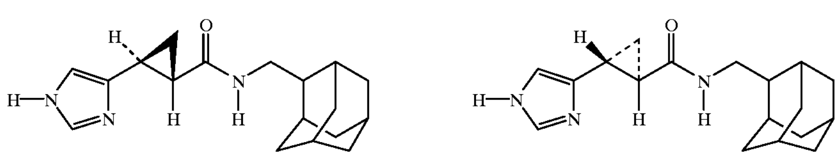 | 55 ± 6 |

TABLE 1-continued

Histamine $H_3$ Receptor Binding Affinities

| Compound | Structure | $H_3$ Receptor $K_i$(nM) |
|---|---|---|
| Example 9 | | 163 ± 19 |
| Example 10 | | 97 ± 21 |
| Example 11 | | 134 ± 13 |
| Example 12 | 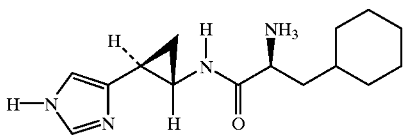 | 1.85 ± 0.5 |
| Example 13 | 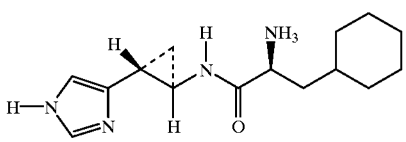 | 21.5 ± 1.8 |
| Example 14 | 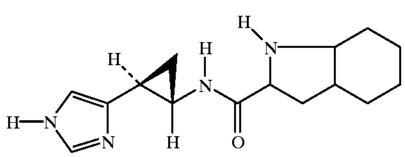 | 8.5 ± 0.7 |
| Example 15 | 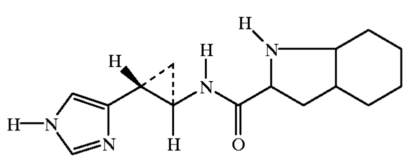 | 37 ± 4 |
| Example 16 | | 12.2 ± 1.0 |
| Example 17 | | 11.0 ± 1.0 |

TABLE 1-continued

Histamine H$_3$ Receptor Binding Affinities

| Compound | Structure | H$_3$ Receptor K$_i$(nM) |
|---|---|---|
| Example 18 | | 240 ± 6.0 |
| Example 19 | | 160 ± 9.0 |
| Example 20 | 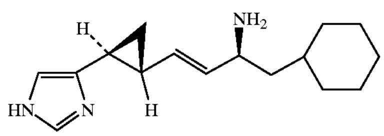 | 0.37 ± 0.2 |
| Example 21 | 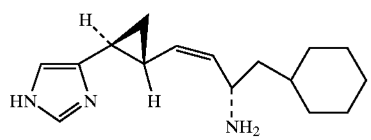 | 97.7 ± 28 |
| Example 22 | 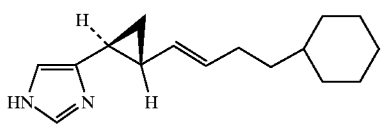 | 2.4 ± 0.2 |
| Example 23 | 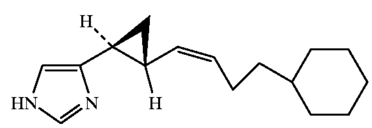 | 6.2 ± 0.8 |
| Example 24 | 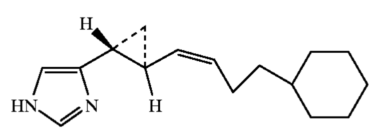 | 108 ± 3.9 |
| Example 25 | 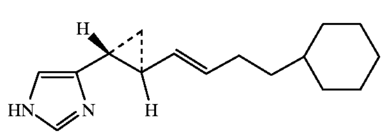 | 56 ± 9.0 |
| Example 26 | | 5.8 ± 0.4 |
| Example 27 | 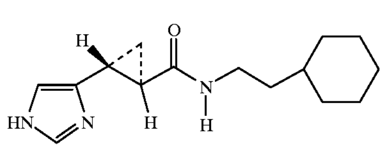 | 8.8 ± 0.1 |

TABLE 1-continued

Histamine H₃ Receptor Binding Affinities

| Compound | Structure | H₃ Receptor $K_i$(nM) |
|---|---|---|
| Example 28 | | 46 ± 13 |
| Example 29 | | 36 ± 8.0 |
| Example 30 | | 42 ± 7.0 |
| Example 31 | | 294 ± 26 |
| Example 32 | | 876 ± 158 |
| Example 33 | | 197 ± 23 |
| Example 34 | | 227 ± 26 |
| Example 35 | | 44 ± 73 |
| Example 36 | | 145 |

TABLE 1-continued

Histamine $H_3$ Receptor Binding Affinities

| Compound | Structure | $H_3$ Receptor $K_i$(nM) |
|---|---|---|
| Example 37 | 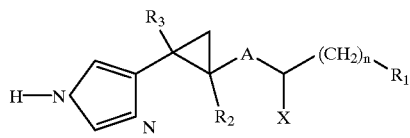 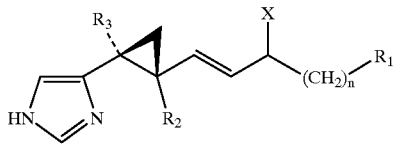 | 68 ± 9.1 |

What is claimed is:

1. A compound of the formula:

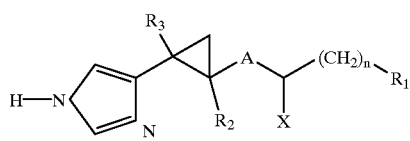

or a pharmaceutically acceptable salt or solvate thereof, wherein:

$R_2$ is a hydrogen or a methyl or ethyl group;

$R_3$ is a hydrogen or a methyl or ethyl group;

n is 0, 1, 2, 3, 4, 5, or 6; and $R_2$ is selected from the group consisting of (a) heterocyclic; (b) decahydronapthalene; and (c) octahydroindene;

with the provisos that when X is $H_1$, A is —CH$_2$CH$_2$—, —COCH$_2$—, —CONH—, —CON(CH$_3$)—, —CH=CH—, —C≡C—, —CH$_2$—NH—, —CH$_2$—N(CH$_3$)—, —CH(OH)CH$_2$—, —NH—CH$_2$—, —N(CH$_3$)—CH$_2$—, —CH$_2$O—, —CH$_2$S—, or —NHCOO—; and when X is NH$_2$, NH(CH$_3$), N(CH$_3$)$_2$, OH, OCH$_3$, CH$_3$, SH, or SCH$_3$; A is —NHCO—, —N(CH$_3$)—CO—, —NHCH$_2$—, —N(CH$_3$)—CH$_2$—, —CH=CH—, —COCH$_2$—, —CH$_2$CH$_2$—, —CH(OH)CH$_2$—, or —C≡C—.

2. A compound of the formula:

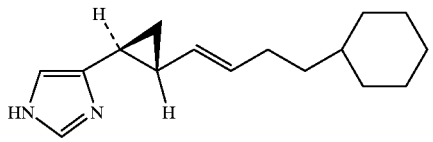

or a pharmaceutically acceptable salt or hydrate thereof, where A is —CONH—, —CH=CH—, —NHCOO—, or —C≡C—;

X is $H_1$, CH$_3$ or NH$_2$;

$R_2$ and $R_3$ are H;

n is 0, 1, 2, or 3; and $R_1$ is phenyl or substituted phenyl.

3. A compound having the formula:

(48.0)

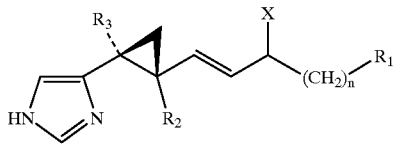

(49.0)

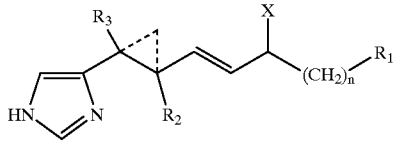

(50.0)

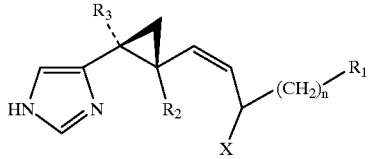

(51.0)

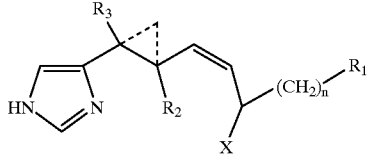

or a pharmaceutically acceptable salt or hydrate thereof, where X is H, CH$_3$ or NH$_2$;

$R_2$ and $R_3$ are H;

n is 0, 1, 2 or 3; and $R_1$ is cyclohexyl, phenyl or substituted phenyl.

4. A compound as in claim 3 having the structure:

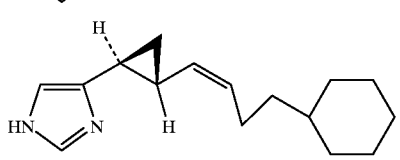

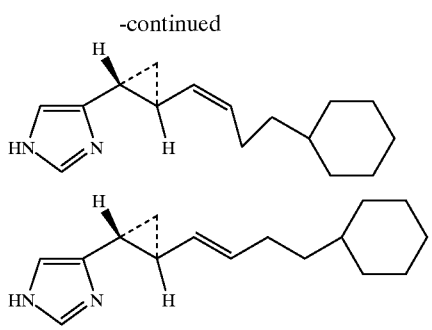

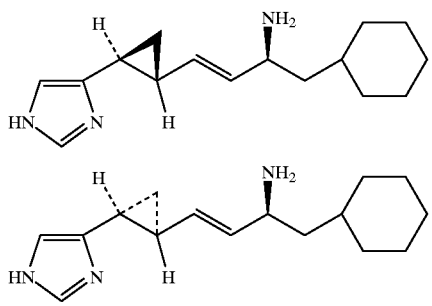

or a pharmaceutically acceptable salt thereof.

5. A compound as in claim 3 having the structure:

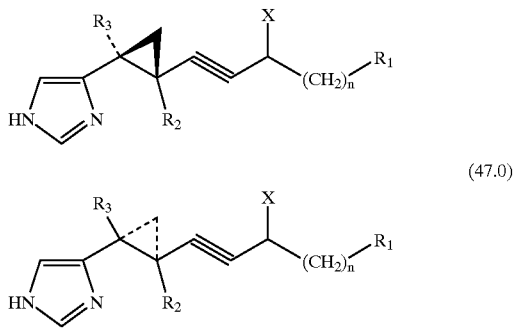

or a pharmaceutically acceptable salt thereof.

6. A compound having the formula:

(46.0)

(47.0)

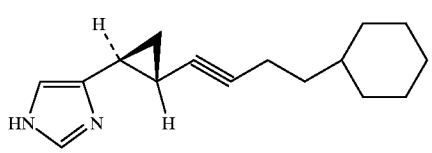

or a pharmaceutically acceptable salt or hydrate thereof, where X is H, $CH_3$, or $NH_2$;

$R_2$ and $R_3$ are H;

n is 0, 1, 2 and 3; and $R_1$ is cyclohexyl, phenyl or substituted phenyl.

7. A compound as in claim 6 having the structure:

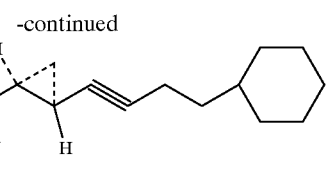

or a pharmaceutically acceptable salt thereof.

8. A compound as in claim 6 having the structure:

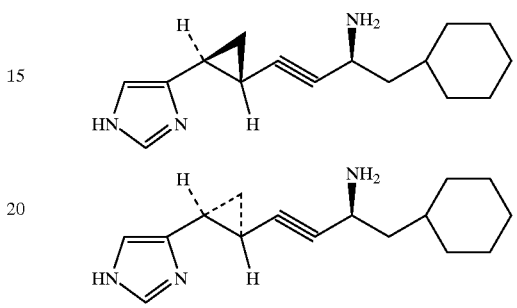

or a pharmaceutically acceptable salt thereof.

9. A compound as in claim 2 having the formula:

(2.0)

(3.0)

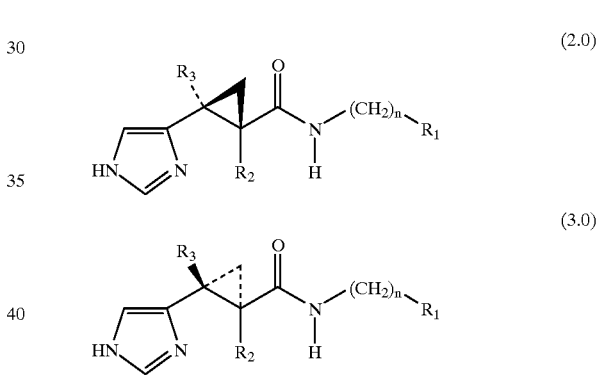

or a pharmaceutically acceptable salt or hydrate thereof, where X is H, $CH_3$, or $NH_2$;

$R_2$ and $R_3$ are H;

n is 0, 1, 2 and 3; and $R_1$ is cyclohexyl, phenyl or substituted phenyl.

10. A compound as in claim 9 having the structure:

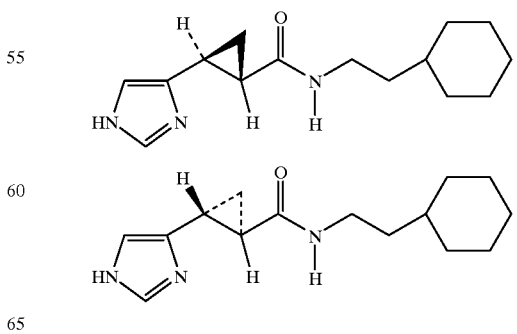

or a pharmaceutically acceptable salt thereof.

11. A compound as in claim 2 having the formula:

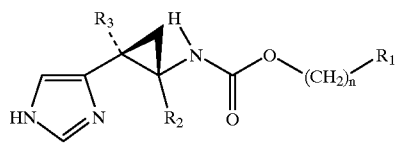
(30.0)

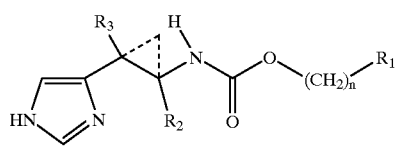
(31.0)

or a pharmaceutically acceptable salt or hydrate thereof, where X is H, CH$_3$, or NH$_2$;
R$_2$ and R$_3$ are H;
n is 0, 1, 2 and 3; and
R$_1$ is cyclohexyl, phenyl or substituted phenyl.

12. A compound as in claim 11 having the structure:

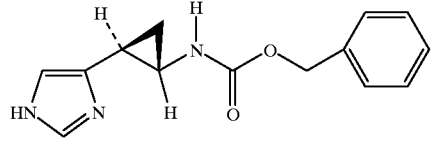

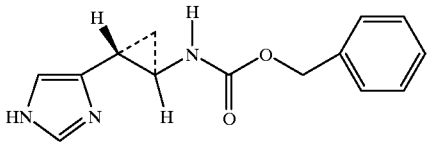

or a pharmaceutically acceptable salt thereof.

13. A pharmaceutical composition comprising at least one compound of claim 1 and a pharmaceutically acceptable carrier.

14. A method of preparing a pharmaceutical composition comprising admixing a compound of claim 1 with a pharmaceutically acceptable carrier.

15. A method of treating CNS disorders involving attention or cognitive disorders comprising administering an effective amount of a compound of claim 1 to a patient in need of such treatment.

* * * * *

UNITED STATES PATENT AND TRADEMARK OFFICE
CERTIFICATE OF CORRECTION

PATENT NO.:      5,990,317

DATED :          November 23, 1999

INVENTOR(S)      Phillips et al.

It is hereby certified that error appear(s) in the above-identified patent and that said Letters Patent hereby corrected as shown below:

Title page, section [75] after Solon, please insert -- Stephen L. Yates, Aurora, --

Signed and Sealed this

Sixth Day of February, 2001

*Attest:*

Q. TODD DICKINSON

*Attesting Officer*      *Director of Patents and Trademarks*